US010813605B2

(12) United States Patent
Arai et al.

(10) Patent No.: US 10,813,605 B2
(45) Date of Patent: Oct. 27, 2020

(54) CT IMAGING APPARATUS, INFORMATION PROCESSING APPARATUS, CT IMAGING METHOD, INFORMATION PROCESSING METHOD, AND RECORDING MEDIUM

(71) Applicants: J. MORITA MANUFACTURING CORPORATION, Kyoto-shi, Kyoto (JP); NIHON UNIVERSITY, Chiyoda-ku, Tokyo (JP)

(72) Inventors: Yoshinori Arai, Tokyo (JP); Hideki Yoshikawa, Kyoto (JP)

(73) Assignees: J. MORITA MANUFACTURING CORPORATION, Kyoto (JP); NIHON UNIVERSITY, Tokyo (JP)

( * ) Notice: Subject to any disclaimer, the term of this patent is extended or adjusted under 35 U.S.C. 154(b) by 31 days.

(21) Appl. No.: 16/104,953

(22) Filed: Aug. 20, 2018

(65) Prior Publication Data
US 2019/0053775 A1  Feb. 21, 2019

(30) Foreign Application Priority Data
Aug. 21, 2017  (JP) .................................. 2017-158774

(51) Int. Cl.
*A61B 6/14* (2006.01)
*A61B 6/00* (2006.01)
(Continued)

(52) U.S. Cl.
CPC ................ *A61B 6/14* (2013.01); *A61B 6/032* (2013.01); *A61B 6/107* (2013.01); *A61B 6/4085* (2013.01);
(Continued)

(58) Field of Classification Search
CPC .. A61B 6/14; A61B 6/54; A61B 6/501; A61B 6/487; A61B 6/032; A61B 6/4085;
(Continued)

(56) References Cited

U.S. PATENT DOCUMENTS 7,197,107 B2   3/2007  Arai et al.
2010/0067650 A1  3/2010  Arai et al.

FOREIGN PATENT DOCUMENTS

EP  2364648 A1  9/2011
EP  2659838 A1  11/2013
(Continued)

OTHER PUBLICATIONS

Search Report from the corresponding European Patent Application No. 18189784.4 dated Mar. 15, 2019.

*Primary Examiner* — David P Porta
*Assistant Examiner* — Gisselle M Gutierrez
(74) *Attorney, Agent, or Firm* — Shinjyu Global IP

(57) ABSTRACT

A first position setting unit receives an operation to designate a position in a mesiodistal on a panoramic tomographic image displayed on a display, and sets a first position on a curved section based on the designation operation. The fluoroscopic imaging information providing unit provides information irradiating a subject with an X-ray beam along a direction having a component of a tangential direction at the first position of the curved section to execute fluoroscopic imaging acquiring a fluoroscopic image to a main body. A second position setting unit receives an operation to designate a position in a buccolingual direction on the fluoroscopic image displayed on the display, and sets a second position in the buccolingual direction based on the designation operation.

14 Claims, 17 Drawing Sheets

(51) Int. Cl.
*A61B 6/10* (2006.01)
*A61B 6/03* (2006.01)

(52) U.S. Cl.
CPC .............. *A61B 6/463* (2013.01); *A61B 6/485* (2013.01); *A61B 6/487* (2013.01); *A61B 6/501* (2013.01); *A61B 6/54* (2013.01); *A61B 6/4435* (2013.01)

(58) Field of Classification Search
CPC ......... A61B 6/485; A61B 6/107; A61B 6/463; A61B 6/4435; A61B 6/4429; A61B 6/44
USPC .......................................................... 378/19
See application file for complete search history.

(56) References Cited

FOREIGN PATENT DOCUMENTS

| | | | |
|---|---|---|---|
| JP | 4163991 | B2 | 8/2008 |
| JP | 4786685 | B2 | 7/2011 |

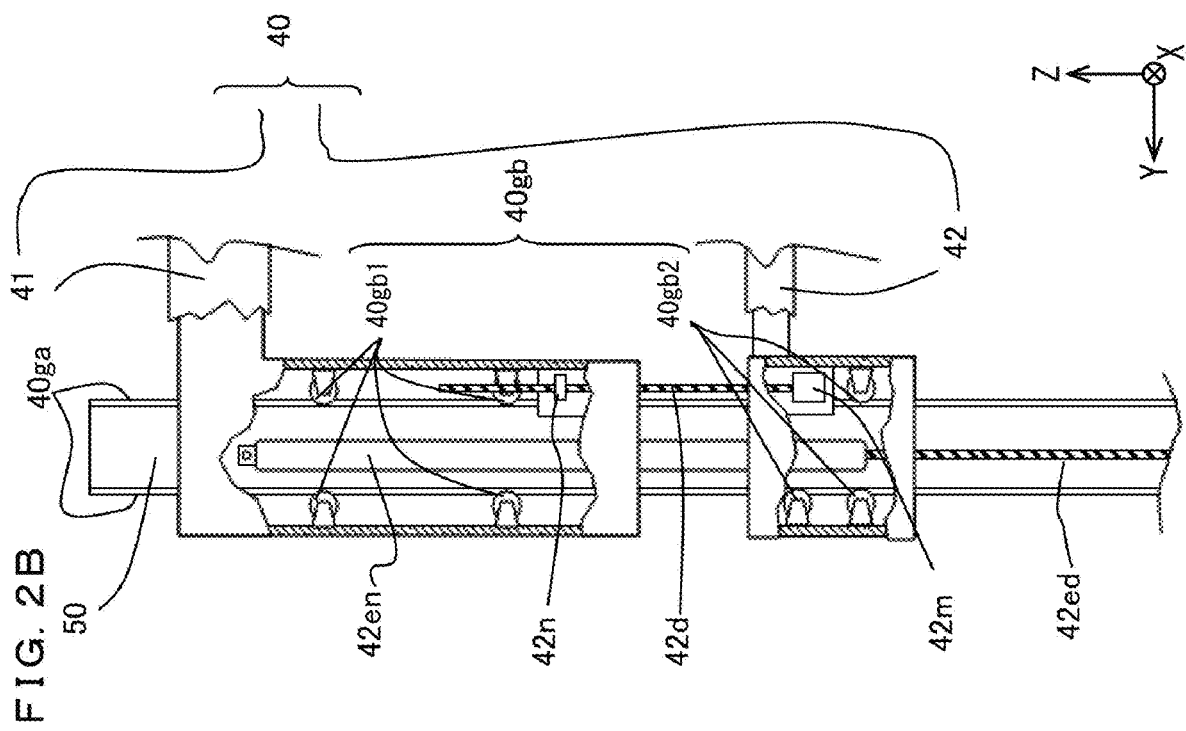
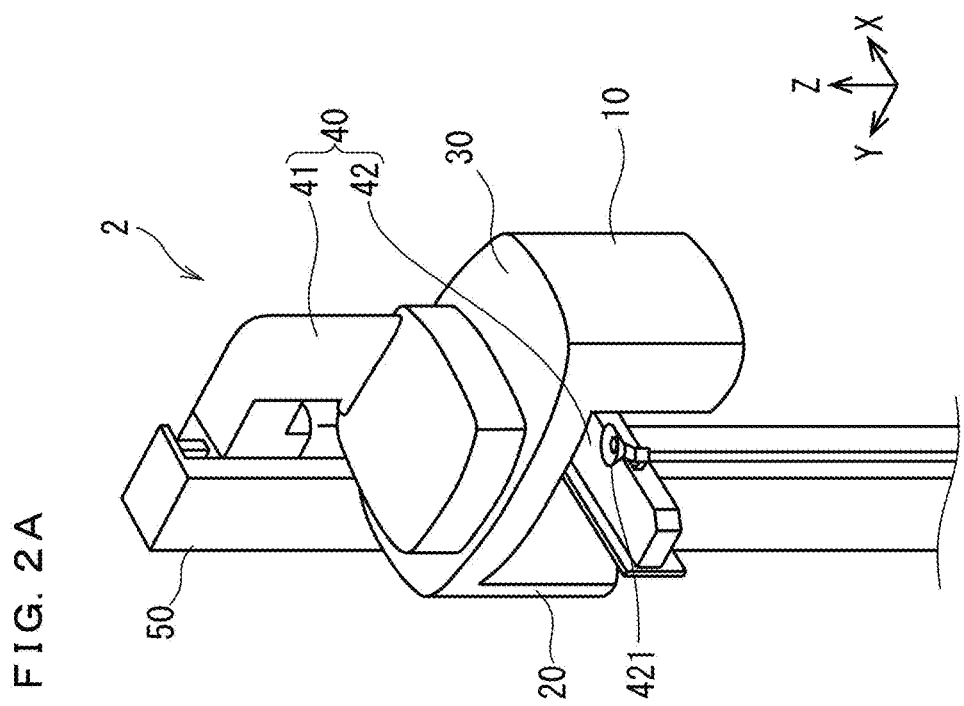

F I G. 1 5
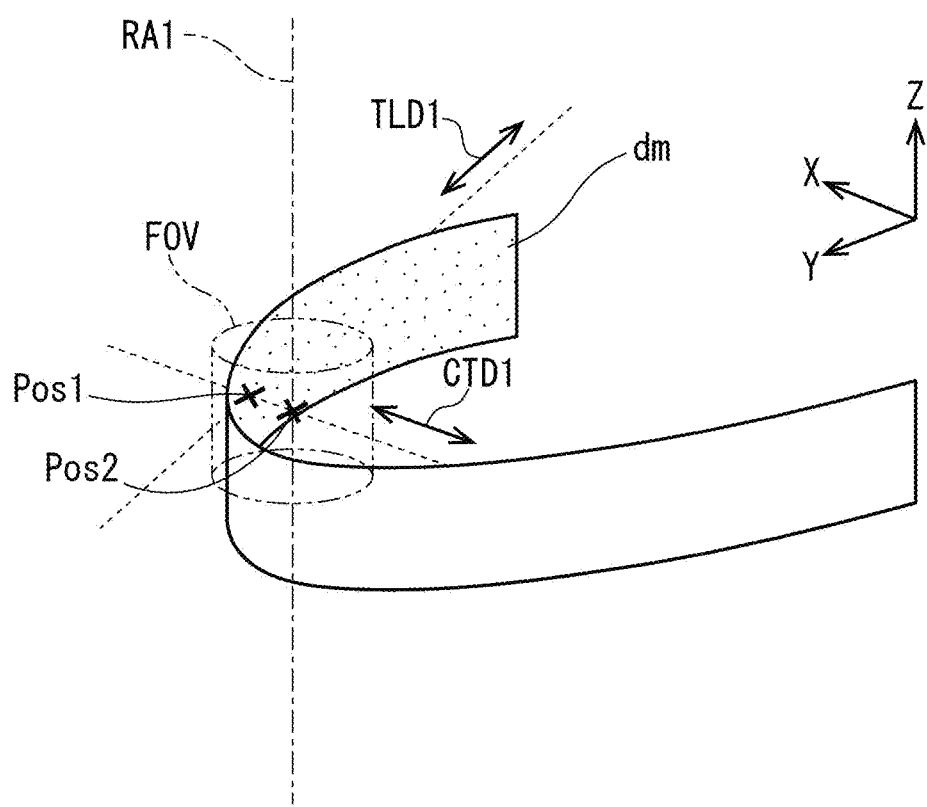

CT IMAGING APPARATUS, INFORMATION PROCESSING APPARATUS, CT IMAGING METHOD, INFORMATION PROCESSING METHOD, AND RECORDING MEDIUM

CROSS-REFERENCE TO RELATED APPLICATIONS

This application claims priority to Japanese Patent Application No. 2017-158774 filed on Aug. 21, 2017. The entire disclosure of Japanese Patent Application No. 2017-158774 is hereby incorporated herein by reference.

TECHNICAL FIELD

Certain implementations refer to a technique of positioning an imaging region of CT imaging.

BACKGROUND

In recent years, in order to suppress an exposure dose, X-ray CT imaging is executed while the imaging region is limited to a local region to irradiate the local region with a narrowed X-ray. In particular, a manipulator positions the imaging region as a region of interest on a panoramic tomographic image while in the panoramic tomographic image of a jaw of a human body is displayed on a screen. Typically, the panoramic tomographic image is often photographed at time of an initial diagnosis of dental examination, so that the panoramic tomographic image acquired at the time of the initial diagnosis can effectively be used for X-ray CT imaging.

SUMMARY

The use of certain panoramic tomographic images can accurately and easily position the imaging region in the mesiodistal direction. However, the panoramic tomographic image has insufficient information about a direction (buccolingual direction) orthogonal to the mesiodistal direction. For this reason, it is difficult to accurately position the imaging region with respect to the buccolingual direction only with the panoramic tomographic image.

The fluoroscopic images taken from the two directions orthogonal to each other may be used, so that the imaging region can three-dimensionally be positioned. However, because the image used for setting is the fluoroscopic image, there is a risk that the position of the region of interest is hardly understood such that a tooth is hidden behind another tooth or a tissue. For this reason, sometimes the imaging region is hardly accurately positioned in the region of interest.

An object of certain implementations is to provide a technique capable of accurately and easily positioning the imaging region of the CT imaging.

Certain implementations are directed to a CT imaging apparatus.

According to a first aspect, a CT imaging apparatus includes: an X-ray generator that emits an X-ray beam; an X-ray detector that detects the X-ray beam; a support that supports the X-ray generator and the X-ray detector while opposing the X-ray generator and the X-ray detector to each other; a rotation driving unit that rotates the support around a rotation axis line located between the X-ray generator and the X-ray detector; a display that displays a panoramic tomographic image that is an image of a curved section corresponding to a dental arch of a subject; a first position setting unit that receives an input of a designation operation to designate a position in a mesiodistal direction on the panoramic tomographic image displayed on the display, and sets a first position on the curved section based on the designation operation; a fluoroscopic imaging executing unit that irradiates the subject with the X-ray beam along a fluoroscopic imaging direction having a component of a tangential direction at the first position on the curved section by controlling the X-ray generator, the X-ray detector, and the rotation driving unit, and acquires a fluoroscopic image; a second position setting unit that receives an input of a designation operation to designate a position in a buccolingual direction on the fluoroscopic image displayed on the display, and sets a second position based on the designation operation; an imaging region setting unit that sets an imaging region of CT imaging based on the second position; and a CT imaging executing unit that irradiates the imaging region set by the imaging region setting unit with an X-ray cone beam by controlling the X-ray generator, the X-ray detector, and the rotation driving unit, and executes the CT imaging.

According to certain implementations, the first position in the mesiodistal direction of the imaging region can be designated on the panoramic tomographic image, which can be observed while the plurality of teeth are laterally spread, so that the manipulator can suitably set the imaging region. The fluoroscopic image in a direction intersecting the first position is acquired by the irradiation of the X-ray in the fluoroscopic imaging direction having the tangential component at the first position in the curved section corresponding to the panoramic tomographic image. The position in the direction intersecting the sectional plane, namely, the position in the buccolingual direction (an inside and outside direction of the dental arch) can be set as the second position by receiving the position designation on the fluoroscopic image. Consequently, the second position in the buccolingual direction, which is hardly set with only the panoramic tomographic image, can suitably be set.

Preferably, the second position setting unit may receive designation to set the second position while the panoramic tomographic image and the fluoroscopic image are displayed in parallel on the display.

According to certain implementations, in receiving the operation to set the second position in the buccolingual direction with respect to the imaging region of the CT imaging, the panoramic tomographic image is displayed on the display in addition to the fluoroscopic image. The position on the dental arch that should be set to the imaging region can be easily checked by displaying the panoramic tomographic image.

Preferably, the second position setting unit may receive the input of the designation operation to set the second position while a position index indicating the first position is displayed on the panoramic tomographic image displayed on the display.

According to certain implementations, in receiving the operation to set the second position in the buccolingual direction with respect to the imaging region of the CT imaging, the position index indicating the first position is displayed on the panoramic tomographic image. Consequently, when setting the imaging region of CT imaging, the operator can easily check the position on the dental arch that should be set to the imaging region using the panoramic tomographic image.

Preferably, the first position setting unit may display a range index indicating a range of the imaging region on the panoramic tomographic image displayed on the display.

According to certain implementations, by displaying the range index indicating the range of the imaging region on the panoramic tomographic image, the first position in the mesiodistal direction of the imaging region can be set such that the region of interest is included in the imaging region.

Preferably, the second position setting unit may display a range index indicating a range of the imaging region on the fluoroscopic image displayed on the display.

According to certain implementations, by displaying the range index indicating the range of the imaging region on the fluoroscopic image, the second position in the buccolingual direction of the imaging region can be set such that the region of interest is included in the imaging region.

Preferably, the fluoroscopic imaging executing unit may acquire a plurality of the fluoroscopic images by irradiating the subject with an X-ray along a plurality of the fluoroscopic imaging directions different from each other, and the second position setting unit may receive the designation operation to set the second position while all or a part of the plurality of the fluoroscopic images is displayed on the display.

According to certain implementations, the operation to designate the position can be performed on the fluoroscopic images acquired from the plurality of directions. Consequently, a tooth row can be checked from different directions, so that the second position in the buccolingual direction of the imaging region can suitably be designated.

Preferably, the second position setting unit may continuously display the plurality of fluoroscopic images on the display while switching the plurality of fluoroscopic images, receives an input operation to stop the continuous display, and receives the input of the designation operation to set the second position.

According to certain implementations, the fluoroscopic images viewed from a plurality of directions are continuously displayed. Consequently, the manipulator can observe the region of interest from various directions. For example, in the fluoroscopic image viewed from one direction, sometimes the region of interest becomes obscure by overlapping with another structure. However, in the fluoroscopic image viewed from another direction, the overlap can be reduced. Consequently, the operator can suitably position the imaging region by selecting the fluoroscopic image favorable to set the position of the imaging region of the CT imaging.

Preferably, the CT imaging apparatus may further include a panoramic imaging executing unit that executes panoramic imaging for acquiring the panoramic tomographic image.

According to certain implementations, the fluoroscopic imaging, the CT imaging, and the panoramic imaging can be executed by one CT imaging apparatus.

Certain implementations are directed to an information processing apparatus.

According to certain implementations, an information processing apparatus that processes information causing an X-ray imaging apparatus to execute X-ray imaging, the information processing apparatus includes: a display that displays a panoramic tomographic image that is an image of a curved section corresponding to a dental arch of a subject; a first position setting unit that receives an input of a designation operation to designate a position in a mesiodistal direction on the panoramic tomographic image displayed on the display, and sets a first position on the curved section based on the designation operation; a fluoroscopic imaging information providing unit that provides information executing X-ray imaging for acquiring a fluoroscopic image by irradiating the subject with an X-ray beam along a fluoroscopic imaging direction having a component of a tangential direction at the first position of the curved section to the X-ray imaging apparatus; a second position setting unit that receives an input of a designation operation to designate a position in a buccolingual direction on the fluoroscopic image that is acquired by the X-ray imaging apparatus and displayed on the display, and sets a second position based on the designation operation; an imaging region setting unit that sets an imaging region of CT imaging based on the second position; and a CT imaging information providing unit that provides information executing the CT imaging by irradiating the imaging region with an X-ray cone beam to the X-ray imaging apparatus capable of executing the CT imaging.

Certain implementations are directed to a CT imaging method.

According to certain implementations, a CT imaging method includes: (A) a step of displaying on a display a panoramic tomographic image that is an image of a curved section corresponding to a dental arch of a subject; (B) a step of receiving an input of a designation operation to designate a position in a mesiodistal direction on the panoramic tomographic image displayed on the display in the step (A), and setting a first position on the curved section based on the designation operation; (C) a step of acquiring a fluoroscopic image by irradiating the subject with an X-ray beam along a fluoroscopic imaging direction having a component of a tangential direction at the first position of the curved section set in the step (B); (D) a step of displaying the fluoroscopic image acquired in the step (C) on the display; (E) a step of receiving an input of a designation operation to designate a position in a buccolingual direction on the fluoroscopic image displayed on the display in the step (D), and setting a second position based on the designation operation; (F) a step of setting an imaging region of CT imaging based on the second position set in the step (E); and (G) a step of executing the CT imaging by irradiating the imaging region set in the step (F) with an X-ray cone beam.

certain implementations are directed to an information processing method for processing information causing an X-ray imaging apparatus to execute X-ray imaging.

According to certain implementations, an information processing method of processing information causing an X-ray imaging apparatus to execute X-ray imaging, the information processing method includes: (a) a step of displaying on a display a panoramic tomographic image that is an image of a curved section corresponding to a dental arch of a subject; (b) a step of receiving an input of a designation operation to designate a position in a mesiodistal direction on the panoramic tomographic image displayed on the display in the step (a), and setting a first position on the curved section based on the designation operation; (c) a step of providing information executing X-ray imaging for acquiring a fluoroscopic image by irradiating the subject with an X-ray beam along a fluoroscopic imaging direction having a component of a tangential direction at the first position of the curved section set in the step (b) to an X-ray imaging apparatus; (d) a step of displaying the fluoroscopic image acquired by the X-ray imaging apparatus on the display; (e) a step of receiving an input of a designation operation to designate a position in a buccolingual direction on the fluoroscopic image displayed on the display in the step (d), and setting a second position based on the designation operation; (f) a step of setting an imaging region of CT imaging based on the second position set in the step (e); and (g) a step of providing information executing the CT imaging by irradiating the imaging region set in the step (f) with an X-ray cone beam to the X-ray imaging apparatus capable of executing the CT imaging.

Certain implementations are directed to a non-transitory recording medium in which a computer-readable program is recorded.

According to certain implementations, a non-transitory recording medium having a computer-readable program recorded on the medium, the program causing a computer to execute: (a) a step of displaying on a display a panoramic tomographic image that is an image of a curved section corresponding to a dental arch of a subject; (b) a step of receiving an input of a designation operation to designate a position in a mesiodistal direction on the panoramic tomographic image displayed on the display in the step (a), and setting a first position on the curved section based on the designation operation; (c) a step of providing information executing X-ray imaging for acquiring a fluoroscopic image by irradiating the subject with an X-ray beam along a fluoroscopic imaging direction having a component of a tangential direction at the first position of the curved section set in the step (b) to the X-ray imaging apparatus; (d) a step of displaying the fluoroscopic image acquired by the X-ray imaging apparatus on the display; (e) a step of receiving an input of a designation operation to designate a position in a buccolingual direction on the fluoroscopic image displayed on the display in the step (d), and setting a second position based on the designation operation; (f) a step of setting an imaging region of CT imaging based on the second position set in the step (e); and (g) a step of providing information executing the CT imaging by irradiating the imaging region set in the step (f) with an X-ray cone beam to the X-ray imaging apparatus capable of executing the CT imaging.

These and other objects, features, aspects and advantages will become more apparent from the following detailed description when taken in conjunction with the accompanying drawings.

BRIEF DESCRIPTION OF THE DRAWINGS

FIG. 2A is a schematic perspective view illustrating a vicinity of an upper portion of a main body 2 of the first embodiment;

FIG. 2B is a view illustrating an internal structure in the vicinity of the upper portion of the main body 2 of the first embodiment while a cover is partially broken away;

FIG. 15 is a view illustrating a setting example of an imaging region FOV;

DETAILED DESCRIPTION

Figure 1:
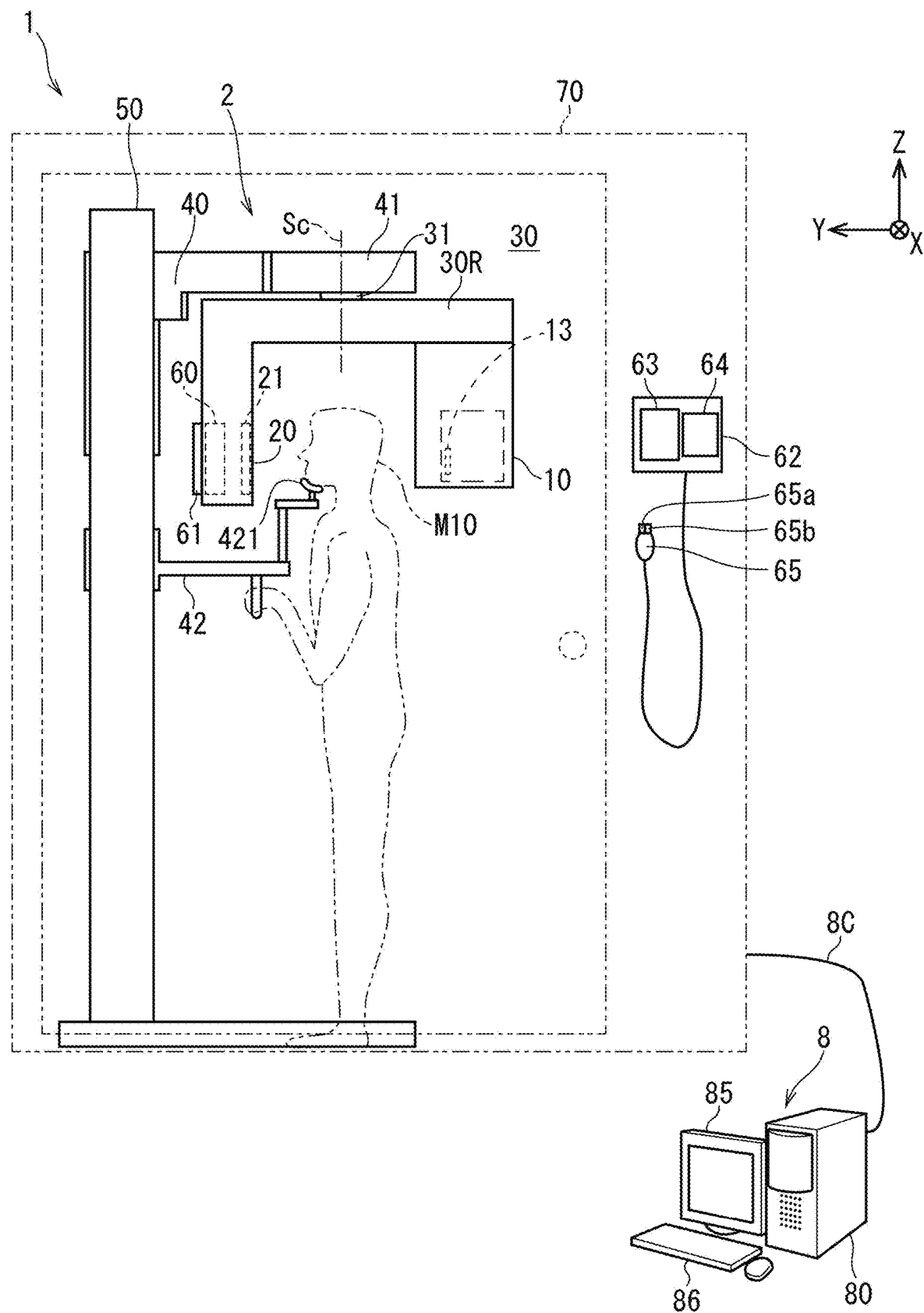
FIG. 1 is a schematic side view illustrating an X-ray imaging apparatus 1 of a first embodiment.

Hereinafter, certain implementations will be described with reference to the accompanying drawings. Constituent elements described in certain implementations are merely examples, but the scope of the present invention is not limited to the constituent elements of the certain implementations. In the drawings, for ease of understanding, sometimes dimensions and the number of each portion may be exaggerated or simplified as necessary.

As used throughout this disclosure, the singular forms "a," "an," and "the" include plural reference unless the context clearly dictates otherwise. Thus, for example, a reference to "a composition" includes a plurality of such compositions, as well as a single composition.

1. First Embodiment

Figure 3:
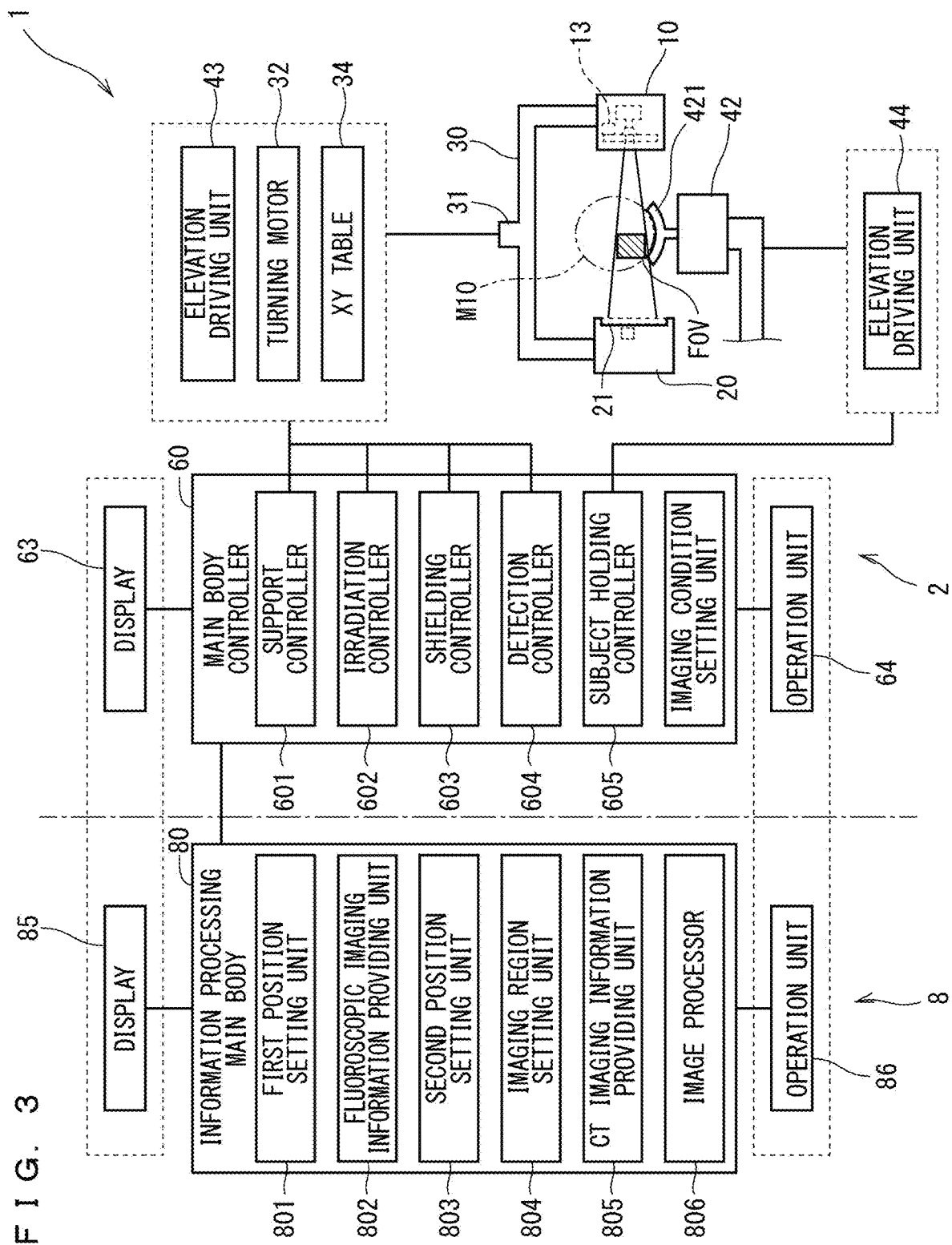
FIG. 3 is a block diagram illustrating a hardware configuration of an information processing apparatus 8 of the first embodiment.
Figure 4:
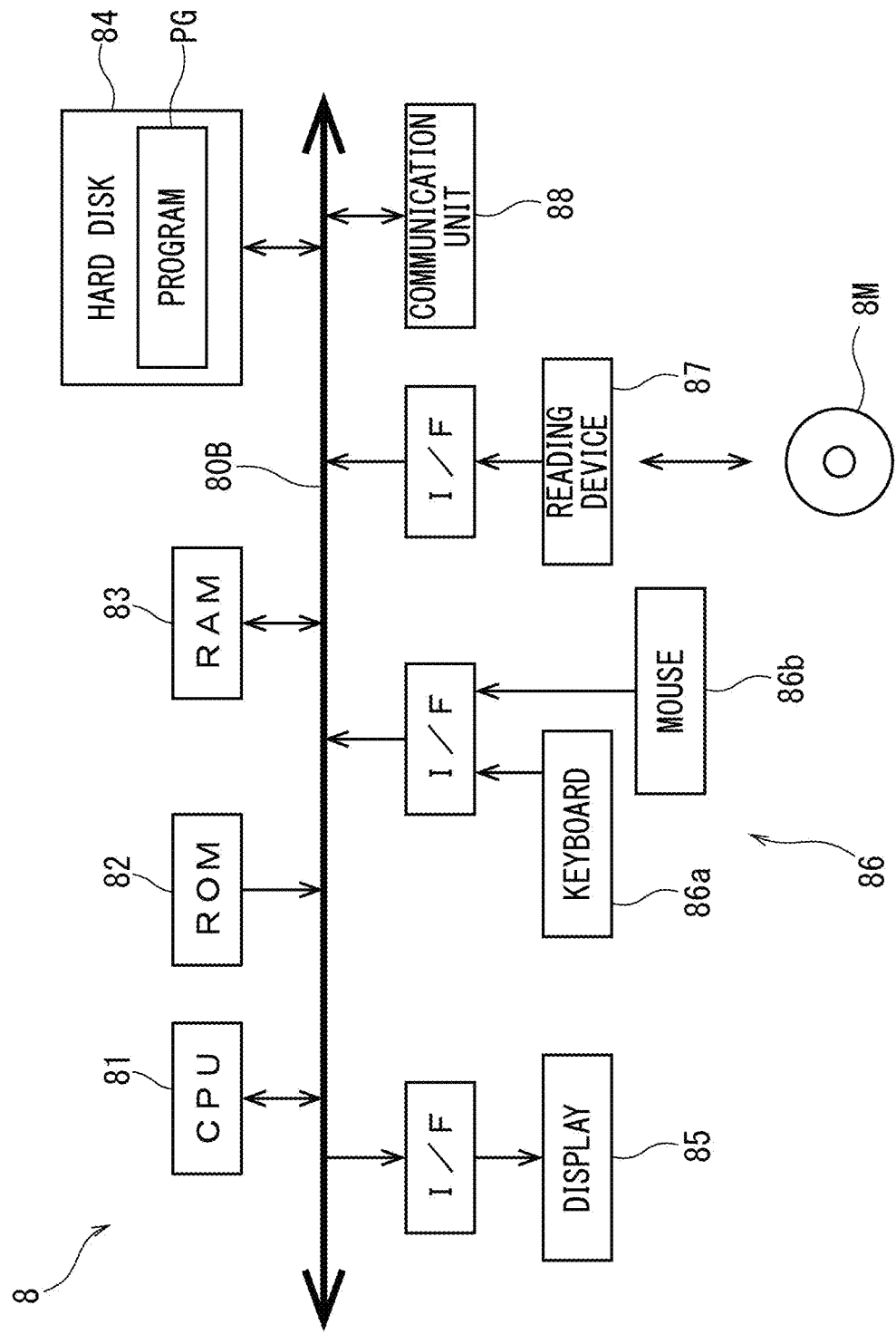
FIG. 4 is a block diagram illustrating a functional configuration of the X-ray imaging apparatus 1 of the first embodiment.

FIG. 1 is a schematic side view illustrating an X-ray imaging apparatus 1 of a first embodiment. FIG. 2A is a schematic perspective view illustrating a vicinity of an upper portion of a main body 2 of the first embodiment. FIG. 2B is a view illustrating an internal structure in the vicinity of the upper portion of the main body 2 of the first embodiment while a cover is partially broken away. FIG. 3 is a block diagram illustrating a hardware configuration of an information processing apparatus 8 of the first embodiment. FIG. 4 is a block diagram illustrating a functional configuration of the X-ray imaging apparatus 1 of the first embodiment.

The X-ray imaging apparatus 1 is a device that photographs a subject using an X-ray. In this case, the subject is a head M10 of an examinee, and the X-ray imaging apparatus 1 has a configuration particularly suitable for imaging a tooth jaw of the head M10. As described later, the X-ray imaging apparatus 1 is a CT imaging apparatus configured to be able to execute fluoroscopic imaging, panoramic imaging, and CT imaging with respect to the head M10.

The X-ray imaging apparatus 1 includes a main body 2 and an information processing device 8. The main body 2 is an apparatus portion that executes X-ray imaging. The information processing apparatus 8 generates information (X-ray imaging information) operating the main body 2, such as an X-ray imaging condition, and executes processing of image information acquired by the X-ray imaging of the main body 2. A main body controller 60 of the main body 2 executes the X-ray imaging according to a program PG. As described later, the main body controller 60 functions as a fluoroscopic imaging executing unit and a CT imaging executing unit. The fluoroscopic imaging executing unit acquires a fluoroscopic image by controlling the X-ray generator 11, the X-ray detector 21, and a rotation driving unit (the turning motor 32). The CT imaging execution unit executes a CT imaging by controlling the X-ray generator 11, the X-ray detector 21, and the rotation driving unit (the turning motor 32)

The main body 2 is accommodated in a hollow rectangular parallelepiped X-ray protective room 70 at an X-ray imaging site. The information processing apparatus 8 is disposed outside the X ray protective room 70. The main unit 2 includes an operation display 61. The operation display 61 and the information processing apparatus 8 are mutually connected by a connection cable 8C.

The main body 2 includes an X-ray generating unit 10, an X-ray detecting unit 20, a turning arm 30, an elevating unit 40, a support post 50, and the main body controller 60. The X-ray generating unit 10 emits an X-ray with which the head M10 is irradiated. The X-ray detecting unit 20 detects the X-ray emitted from the X-ray generating unit 10. The turning arm 30 is a support that supports the X-ray generating unit 10 and the X-ray detecting unit 20 in an opposing state. The elevating unit 40 rises and falls along the support post 50 extending in a vertical direction. The turning arm 30 is supported by an upper frame 41 of the elevating unit 40. Hereinafter, a configuration of each unit will be described in detail.

Sometimes each drawing including FIG. 1 may have a right-handed XYZ rectangular coordinate system. At this point, a direction parallel to an axial direction of a turning axis (rotation axis) 31 of the turning arm 30 (in this case, the vertical direction) is referred to as a Z-axis direction, a direction intersecting the Z-axis direction is referred to as an X-axis direction, and a direction intersecting the X-axis direction and the Z-axis direction is referred to as a Y-axis direction. The X-axis direction and the Y-axis direction can be decided in any way. However, in this case, when the examinee is positioned in the X-ray imaging apparatus 1 to directly face the support post 50, a left and right direction of the examinee is defined as the X-axis direction, and a back and forth direction of the examinee is defined as the Y-axis direction. In the first embodiment, a right-hand direction is set to a (+X) direction, a front direction is set to a (+Y) direction, and a vertically upward direction is set to a (+Z) direction when viewed from the examinee directly facing the post 50.

In the following description, sometimes the Z-axis direction is referred to as the vertical direction, and a direction on a plane defined by two dimensions of the X-axis direction and the Y-axis direction is referred to as a horizontal direction. In the following description, X, Y, Z may be used to define a two-dimensional coordinates or a plane. For example, a two-dimensional coordinate constructed with an X coordinate and a Y coordinate is set to an XY coordinates, and a two-dimensional plane spreading in an X direction and a Y direction is set to an XY plane.

<X-Ray Generating Unit 10>

The X-ray generating unit 10 includes an X-ray generator 11 and a beam shaping mechanism 13.

The X-ray generator 11 includes an X-ray tube that is an X-ray source that generates the X-ray. Intensity (output intensity) of an X-ray beam emitted from the X-ray generator 11 can be controlled by changing the voltage and/or the current supplied to the X-ray tube. The X-ray generator 11 is controlled by an irradiation controller 602 of the main body controller 60.

The beam shaping mechanism 13 partially shields the X-ray beam emitted from the X-ray generator 11, thereby forming the X-ray beam having a shape corresponding to an imaging purpose (an X-ray cone beam or an X-ray narrow beam). That is, the beam shaping mechanism 13 controls an X-ray imaging region with respect to the head M10. The beam shaping mechanism 13 is controlled by a shielding controller 603.

For example, the beam shaping mechanism 13 may be constructed with an X-ray shielding member (not illustrated) disposed close to the X-ray generator 11 and a moving mechanism (not illustrated) that moves the X-ray shielding member. For example, the X-ray shielding member may be constructed with a single plate member in which a plurality of openings having different opening shapes are provided, or at least two shielding members in which an opening having a required size or shape is formed by moving in an approaching or separating direction. For example, the moving mechanism may be constructed with a ball screw mechanism or a linear motor mechanism.

<X-Ray Detecting Unit 20>

The X-ray detecting unit 20 includes an X-ray detector 21. The X-ray detector 21 detects an X-ray beam emitted from the X-ray generator 11. The X-ray detector 21 includes a detection surface constructed with a plurality of arrayed detection elements. For example, the X-ray detector 21 may be constructed with a flat panel detector (FPD) or an X-ray fluorescence intensifier (Image Intensifier (I.I.)).

The plurality of detection elements arrayed on the detection surface of the X-ray detector 21 convert the intensity of the incident X-ray into an electric signal. The electric signal is output as an image signal to the main body controller 60 or the information processing device 8, and an X-ray image is generated based on the image signal.

The X-ray detector 21 is attached to a side portion of a casing of the X-ray detecting unit 20, the side portion facing the X-ray generator 11, and the detection surface is irradiated with the X-ray beam emitted from the X-ray generator 11.

<Turning Arm 30>

The X-ray generating unit 10 and the X-ray detecting unit 20 are fixed to both ends of the turning arm 30 in a suspended state, and are supported so as to be opposed to each other. The turn arm 30 is supported in the suspended state by the elevating unit 40 while a turning shaft 31 extending in the vertical direction is interposed therebetween. In the state in which the X-ray generating unit 10 and the X-ray detecting unit 20 are attached, the turning arm 30 has a substantially inverted U-shape in front view, and turns about a rotation axis line Sc that is a center of the turning shaft 31 provided at an upper end of the turning arm 30. The rotation axis line Sc is a line along the Z direction. The rotation axis line Sc is located between the X-ray generator 11 and the X-ray detector 21.

In this embodiment, a support supporting the X-ray generating unit 10 and the X-ray detecting unit 20 is constructed with the turning arm 30. However, the support may be in other forms. For example, it is conceivable that an annular member in which an outer circumference fixed to the upper portion of the head M10 is rotatably engaged with an outer circumferential portion of a circular member with a ball bearing interposed therebetween is used instead of the turning arm 30. In this case, the X-ray generating unit 10 and the X-ray detecting unit 20 are attached to the annular member so as to be opposed to each other. By circumferentially moving the annular member on the outer circumferential portion of the circular member, the X-ray generating unit 10 and the X-ray detecting unit 20 can be rotated about the head M10 while the head M10 is sandwiched therebetween.

<Elevating Unit 40>

The elevating unit 40 is engaged with the support post 50, and configured to be movable in the vertical direction with respect to the support post 50. The support post 50 is a member having a length in the vertical direction. The elevating unit 40 includes an upper frame 41, a lower frame 42, and elevation driving units 43, 44. The upper frame 41 and the lower frame 42 are engaged with a support post 50 extending in the vertical direction. The elevation driving units 43, 44 include a driving source such as a motor, and the elevation driving unit 43 vertically moves the upper frame 41 along the support post 50, and the elevation driving unit 44 vertically moves the lower frame 42 along the support post 50.

The upper frame 41 extends toward a front side (−Y side) in front view. The turning shaft 31 extending downward is attached to a portion near a leading end of the upper frame 41. The upper frame 41 supports the turning arm 30 in the suspended state with the turning shaft 31 interposed therebetween. As the upper frame 41 moves vertically along the support post 50, the turning arm 30 moves vertically.

For example, as a structure that turns the turning arm 30, preferably the turning shaft 31 is fixed to the upper frame 41 in a non-rotatable manner, and the turning arm 30 is turnably attached to the turning shaft 31. In this case, the turning arm 30 turns with respect to the non-rotatable turning shaft 31. The turning shaft 31 may be rotatably attached to the upper frame 41 while the turning arm 30 is coupled to the turning shaft 31 in the non-rotatable manner. In this case, the turning arm 30 turns by rotating the turning shaft 31.

In the former, for example, torque of a turning motor 32 is preferably applied to the turning arm 30 by a power transmission mechanism (not illustrated) such as a belt and a pulley. For example, the turning motor 32 is fixed to the inside of the turning arm 30, and an annular belt is entrained about both a pulley fixed to a rotation shaft of the turning motor and the turning shaft 31, whereby rotation driving force of the turning motor 32 may be applied to the turning arm 30. In this case, a bearing member such as a bearing may be interposed between the turning shaft 31 and the turning arm 30.

The turning motor 32 may be provided in the upper frame 41. In this case, a belt (not illustrated), a pulley (not illustrated), or a rotation shaft (not illustrated) passing through the inside of the turning shaft 31 may be provided as a transmission mechanism that transmits power of the turning motor 32. In this case, the turning arm 30 is preferably turned by transmitting the rotation driving force of the turning motor 32 to the turning arm 30.

In the latter, the turning motor 32 is installed in the upper frame 41, and the rotation driving force of the turning motor 32 may be applied to the turning shaft 31 while a transmission mechanism (not illustrated) such as a roller is interposed therebetween. In this case, a bearing member such as a bearing may be interposed between the turning shaft 31 and the upper frame 41.

In this embodiment, the turning shaft 31 is disposed so as to extend in the vertical direction. Alternatively, it is conceivable that the turning shaft 31 is inclined at an arbitrary angle with respect to the vertical direction. For example, in the case that the turning shaft 31 is disposed so as to extend in the horizontal direction, the rotation of the turning shaft 31 and the turning arm 30 causes the X-ray generating unit 10 and the X-ray detecting unit 20 to rotate in a plane parallel to the vertical direction.

The transmission mechanism including the turning shaft 31, the bearing, the belt, the pulley, and the rotation shaft and the turning motor 32 are an example of the rotation driving unit that rotates the turning arm 30. That is, the rotation driving unit is a mechanism that relatively turns the turning arm 30 (support) about the turning shaft 31 with respect to the head M10.

The main body 2 includes a horizontal moving unit (not illustrated) that moving the turning arm 30 relative to the head M10 in a direction perpendicular to the turning shaft 31 (the X direction, the Y direction, or a combined direction having both X and Y direction components). The horizontal moving unit may be constructed with an XY table 34 fixed to the upper frame 41 or the turning arm 30. The XY table 34 may be constructed with a table member that moves in the X-axis direction, a table member that moves in the Y-axis direction, and motors that move these table members in the X-axis direction or the Y-axis direction.

In the case that the XY table 34 is fixed to the upper frame 41, the XY table 34 may be fixed to the upper end of the turning shaft 31. In this case, the turning arm 30 and the turning shaft 31 move in the direction (horizontal direction) perpendicular to the turning shaft 31 by driving the XY table 34. In the case that the XY table 34 is fixed to the turning arm 30, the XY table 34 may be fixed to the lower end of the turning shaft 31. In this case, only the turning arm 30 moves in the direction (horizontal direction) perpendicular to the turning shaft 31.

The turning shaft 31 and the turning arm 30 or the turning arm 30 can horizontally be moved by driving the XY table 34 during the turning of the turning arm 30. Consequently, turning centers of the X-ray generating unit 10 and the X-ray detecting unit 20 can be set to a location different from the turning axis 31 that is a mechanical turning center.

For example, in the CT imaging, when the X-ray generating unit 10 and the X-ray detecting unit 20 are looked down from the +Z side, the center of an imaging region FOV (Field of View) is set on the straight line connecting the centers of the X-ray generating unit 10 and the X-ray detecting unit 20. The turning shaft 31 is set on the straight line connecting the centers of the X-ray generating unit 10 and the X-ray detecting unit 20. However, the turning shaft 31 is set at a position different from the center of the imaging region FOV. On such geometrical conditions, the turning arm 30 is turned about the turning axis 31, and the XY table 34 turns the turning shaft 31 about the center of the imaging region FOV by the same angle as a turning angle of the turning arm 30. Consequently, the imaging region FOV is irradiated with an X-ray cone beam while the X-ray generating unit 10 and the X-ray detecting unit 20 turn with the center of the imaging region FOV as the turning center (rotation axis line), which allows the execution of the CT imaging.

The XY table 34 can relatively move the turning arm 30 in the horizontal direction with respect to the head M10. However, a whole or a part of the examinee including the head M10 may horizontally be moved instead of moving the turning arm 30 in the horizontal direction.

A subject holder 421 is provided in the lower frame 42. In this case, the subject holding unit 421 includes a chin rest that holds a jaw of the head M10 and a head holder (not illustrated) that positions the head M10 while the head M10 is sandwiched from both sides of the head M10 (see FIG. 7). The subject holder 421 may have a different configuration. For example, the subject holder 421 may include a bite block to which the head M10 is fixed by chewing of the examinee. By fixing the head M10 to the object holder 421, the head M10 is fixed such that the front-back direction of the head M10 becomes parallel or substantially parallel to the Y-axis direction. That is, in the state in which the head M10 is fixed, a midsagittal section of the head M10 becomes parallel or substantially parallel to the YZ plane defined by the Y-axis direction and the Z-axis direction.

The turning arm 30 is disposed at a proper position by elevating the upper frame 41 according to a height of the examinee. The lower frame 42 also elevates according to the upper frame 41, whereby the head M10 is held by the subject holder 421 provided in the lower frame 42.

As illustrated in FIG. 2B, a motor (not illustrated) is fixed to a support post base, and a driving shaft 42ed such as a male screw is connected to the motor. A bearing member 42en such as a female screw is fixed to the upper frame 41 constituting the elevating unit 40. The driving shaft 42ed is screwed in the bearing member 42en. The upper frame 41 is elevated in the Z-axis direction together with the bearing member 42en by the turning of the driving shaft 42ed.

A motor 42m is fixed to the lower frame 42, and the motor 42m is connected to a driving shaft 42d such as a male screw. A bearing member 42n such as a nut is fixed to the upper frame 41, and the driving shaft 42d is screwed in the bearing member 42n. The upper frame 41 and the lower frame 42 are connected to each other with the driving shaft 42d interposed therebetween.

A guide member 40ga, such as a rail, which guides the elevating unit 40, is fixed to the support post 50. A guided member 40gb1 such as a roller is fixed to the upper frame 41. A guided member 40gb2 such as a roller is fixed to the lower frame 42. The guided member 40gb1 and the guided member 40gb2 constitute a guided member 40gb. The guided member 40gb is guided in the Z-axis direction along the guide member 40ga. When only the driving shaft 42ed is driven without driving the driving shaft 42d, both the upper frame 41 and the lower frame 42 rise and fall, namely, the entire elevating unit 40 rises and falls. The lower frame 42 moves up and down in the Z-axis direction with respect to the upper frame 41 by driving the driving shaft 42d using the motor 42m.

With this structure, for example, the rise of the upper frame 41 by driving the driving shaft 42ed and the fall of the lower frame 42 with respect to the upper frame 41 by driving the driving shaft 42d are synchronized with each other with an identical displacement amount, which allows only the upper frame 41 to rise while the height of the lower frame 42 is kept constant.

For the fall, contrary to the above rise, the fall of the upper frame and the rise of the lower frame 42 with respect to the upper frame 41 are synchronized with each other with the identical displacement amount, which allows only the frame 41 can fall while the height of the lower frame 42 is kept constant.

With such a configuration, for example, in the case that the CT imaging is executed by horizontal irradiation of the X-ray cone beam, the height of the irradiation central axis of the X-ray cone beam can be changed while the height of the head is kept constant.

The imaging region FOV can horizontally be irradiated with the X-ray cone beam in the CT imaging, and the imaging region FOV can be irradiated with the X-ray narrow beam such that the X-ray narrow beam is shot up in the panoramic imaging. In the CT imaging, the imaging region FOV can be irradiated with the X-ray cone beam such that the X-ray cone beam is shot up or such that the X-ray cone beam is shot down. The turning motor 32, the XY table 34, and the elevation driving unit 43 are controlled by a support controller 601 of the main body controller 60 (see FIG. 3). The elevation driving unit 44 that elevates the lower frame 42 is controlled by a subject holding controller 605.

The motor (not illustrated) fixed to the above support post base, the driving shaft 42ed, and the bearing member 42en are a configuration example of the elevation driving unit 43. The motor (not illustrated) fixed to the above support post base, the driving shaft 42ed, the bearing member 42en, the motor 42m, the driving shaft 42d, and the bearing member 42n are a configuration example of the elevation drive unit 44.

<Main Body Controller 60>

The main body controller 60 is a device that controls the main body 2. The main body controller 60 can be constructed with hardware as a computer including a CPU, a ROM, and a RAM (not illustrated). In this case, as illustrated in FIG. 1, the main body controller 60 is installed in the X-ray detecting unit 20.

Buttons for inputting various commands to the main body controller 60 or the operation display 61 constructed with a touch panel on which various pieces of information are displayed is attached to the outer wall surface of the X-ray detector 20 in which the main body controller 60 is provided.

An operation display 62 that inputs each command to the main body controller 60 is also attached to the wall surface of the X-ray protective room 70. The operation display 62 includes a display 63 that displays various pieces of information, an operation unit 64, and a switch 65. The switch 65 includes an imaging start switch 65a that inputs an instruction to start the imaging and a forced termination switch 65b that forcibly terminates the imaging.

A manipulator (for example, an operator) can manipulate the main body 2 through the operation displays 61, 62. However, operation contents and display contents may be different between the operation displays 61, 62 may be different from each other in an operation content and a display content. A part or all of the operation contents and display contents may be common between the operation displays 61, 62.

One of the operation displays 61, 62 may be eliminated. For example, the operation display 62 may be eliminated in the case that the X-ray protective room 70 is eliminated. Although the display content or the operation content of the operation display 62 will be described below, the same holds true for the operation display 61.

The operation display 62 may be used in not only the selection of the X-ray imaging mode but also the setting of the position of the imaging region FOV.

As illustrated in FIG. 3, the main body controller 60 includes the support controller 601, the irradiation controller 602, the shielding controller 603, a detection controller 604, and the subject holding controller 605. Each controller is a function implemented by the operation of the CPU according to a controlling application. A part or all of these functions may be implemented using a dedicated circuit in a by hardware manner.

The support controller 601 controls the turning arm 30 by controlling the turning motor 32. In particular, the support controller 601 rotates the X-ray generating unit 10 and the X-ray detecting unit 20, which are supported by the turning arm 30, about the turning shaft 31, thereby changing an irradiation angle of the X-rays with respect to the head M10. The support controller 601 also controls the movement in the X and Y directions of the turning arm 30 by controlling the XY table 34. The support controller 601 also moves the turning arm 30 together with the upper frame 41 in the Z direction by controlling the elevation driving unit 43.

The irradiation controller 602 controls the X-ray generator 11 of the X-ray generating unit 10. For example, the irradiation controller 602 controls turn-on and -off the X-ray beam emitted from the X-ray generator 11 and the intensity of the X-ray beam by controlling the voltage or current supplied to the X-ray tube of the X-ray generator 11.

The shielding controller 603 controls a shielding amount of the X-ray beam by controlling the beam shaping mechanism 13. The shielding controller 603 forms the X-ray beam (for example, the X-ray narrow beam and the X-ray cone beam) having a shape corresponding to the imaging purpose by the shielding control of the X-ray beam. The shielding controller 603 prevents the region other than the imaging region FOV of the examinee from being irradiated with the X-ray beam by the shielding control of the X-ray beam.

The shielding controller 603 can perform the shielding control for changing the irradiation direction of the X-ray beam using the beam shaping mechanism 13. For example, the horizontal irradiation of the X-ray beam can be performed by equalizing the shielding amount on the upper side of the X-ray beam with the shielding amount on the lower side of the X-ray beam, the X-ray beam can be shot up by decreasing the shielding amount on the upper side of the X-ray beam while increased the shielding amount on the lower side of the X-ray beam, and the X-ray beam can be shot down by increasing the shielding amount on the upper side of the X-ray beam while decreased the shielding amount on the lower side of the X-ray beam.

The X-ray detector 21 may include a detection surface having an area enough to receive the X-ray beam even if the irradiation direction of the X-ray beam is changed. Alternatively, the X-ray detector 21 having a relatively small detection surface may be configured to be able to rise and fall in the X-ray detecting unit 20 using an X-ray detector elevating mechanism (not illustrated). In this case, the X-ray detector 21 (detection surface) preferably rises and falls according to the vertical change in the irradiation direction of the X-ray beam.

The detection controller 604 controls the operation of the X-ray detector 21. For example, the detection controller 604 controls a collimator (secondary X-ray shielding unit) (not illustrated) provided on the front face of the X-ray detector 21. The collimator includes a plate-shaped member, in which a plurality of holes having a plurality of different shapes corresponding to the shape of the X-ray beam are made, in order to partially shield the unnecessary scattered X-ray. The detection controller 604 controls the collimator such that the hole suitable for the imaging purpose is selectively disposed on the detection surface among the plurality of holes.

The subject holding controller 605 moves the subject holder 421 together with the lower frame 42 in the Z direction by controlling the elevation driving unit 44. The subject holding controller 605 can hold the head M10 at a position suitable for the imaging by positioning the subject holder 421 in the Z direction.

As described above, the elevation movement in the Z direction of the upper frame 41 and the turning arm 30 using the elevation driving unit 43 by the control of the support controller 601 is synchronized with the elevation movement in the Z direction of the lower frame 42 and the subject holder 421 using the elevation driving unit 44 by the control of the subject holding controller 605, which allows the position in the Z direction of the turning arm 30 to be changed with respect to the subject holder 421 while the subject holder 421 is kept at the identical position in the Z direction.

<Information Processing Apparatus 8>

As illustrated in FIG. 1, the information processing apparatus 8 includes an information processing body 80, a display 85, and an operation unit 86. As illustrated in FIG. 4, the information processing body 80 includes a CPU 81, a ROM 82, and a RAM 83. The CPU 81 includes an arithmetic circuit that executes various arithmetic operations. The ROM 82 stores a basic program. The RAM 83 is a volatile main storage device that stores various pieces of information. The information processing apparatus 8 has a configuration of a typical computer system in which the CPU 81, the ROM 82, and the RAM 83 are connected by a bus line 80B.

The information processing body 80 further includes a hard disk 84, a reading device 87, and a communication unit 88. These elements are also connected to the bus line 80B through a suitable interface (I/F). The display 85 and the operation unit 86 are also connected to the bus line 80B.

The hard disk 84 is an auxiliary storage device that stores information. The display 85 displays various pieces of information such as an image. The operation unit 86 is an input device including a keyboard 86*a* and a mouse 86*b*. The manipulator can input various instructions to the information processing body 80 through the operation unit 86. The display 85 may be constructed with a touch panel. In this case, the display 85 can also function as the operation unit 86.

The reading device 87 reads information from a computer-readable non-transitory recording medium 8M such as an optical disk, a magnetic disk, and magneto-optical disk. The communication unit 88 transmits and receives a signal to and from an element of the X-ray imaging apparatus 1 or other elements.

The information processing device 8 reads the program PG from the recording medium 8M through the reading device 87, and records the program PG in the hard disk 84. Then, the program PG recorded in the hard disk 84 is copied to the RAM 83. The CPU 81 executes arithmetic processing according to the program PG stored in the RAM 83. In relation to the foregoing description, the CPU 81 can receive operations via the operation unit 86. The operation is received by receiving the input of the operation, strictly speaking, by receiving the signal based on the operation.

As illustrated in FIGS. 1 and 3, the information processing main body 80 functions as a first position setting unit 801, a fluoroscopic imaging information providing unit 802, a second position setting unit 803, an imaging region setting unit 804, a CT imaging information providing unit 805, and an image processor 806. These units are functions implemented in a software manner by the operation of the CPU 81 according to the program PG. A part or all of these units may be implemented in a hardware manner by a dedicated circuit.

The first position setting unit 801 and the second position setting unit 803 are provided to set the position of the imaging region FOV when the CT imaging is executed in the main body 2.

The first position setting unit 801 receives an operation to designate the position in a mesiodistal (mesio-distal) direction on a panoramic tomographic image while the panoramic tomographic image is displayed on the display 85. The panoramic tomographic image is an image of a curved section corresponding to a dental arch in the head M10. The first position setting unit 801 sets the position (first position Pos1) in the mesiodistal direction on the curved section based on the received designation operation. The mesiodistal direction means a direction approaching a median (between the leftmost and rightmost teeth in the dental arch) or a direction away from the median. The first position setting unit 801 also receives an operation to designate the position in the Z direction when receiving the operation to designate the position in the mesiodistal direction on the panoramic tomographic image.

The fluoroscopic imaging information providing unit 802 provides information executing the fluoroscopic imaging to the main body controller 60. In the fluoroscopic imaging, the tangential direction at the first position Pos1 of the curved section set by the first position setting unit 801 is set to a fluoroscopic imaging direction, and the head M10 is irradiated with the X-ray beam to acquire a fluoroscopic image.

The second position setting unit 803 receives the operation designate the position in a buccolingual (bucco-lingual) direction on the fluoroscopic image while the fluoroscopic image is displayed on the display 85. The second position setting unit 803 sets the position (second position Pos2) in the buccolingual direction based on the received designation operation. The buccolingual direction is a direction toward the inside (lingual side) of the dental arch or a direction toward the outside (buccal side (a lip side according to a region)) of the dental arch, and is a horizontal direction orthogonal to the mesiodistal direction.

The imaging region setting unit 804 sets the imaging region FOV of the CT imaging based on the second position Pos2 set by the second position setting unit 803.

The CT imaging information providing unit 805 provides information executing the CT imaging to the main body controller 60. In the CT imaging, the imaging region FOV set by the imaging region setting unit 804 is irradiated with the X-ray cone beam.

When the X-ray imaging is executed in the main body 2, the image processor 806 generates an X-ray image by processing X-ray projection data based on the image signal outputted by the X-ray detector 21. For example, in the case that the CT imaging is executed in the main body 2, the image processor 806 executes various pieces of image processing such as back projection processing and filtering on the projection data, thereby reconstructing the CT image of the designated section.

Description of Operation

Figure 5:
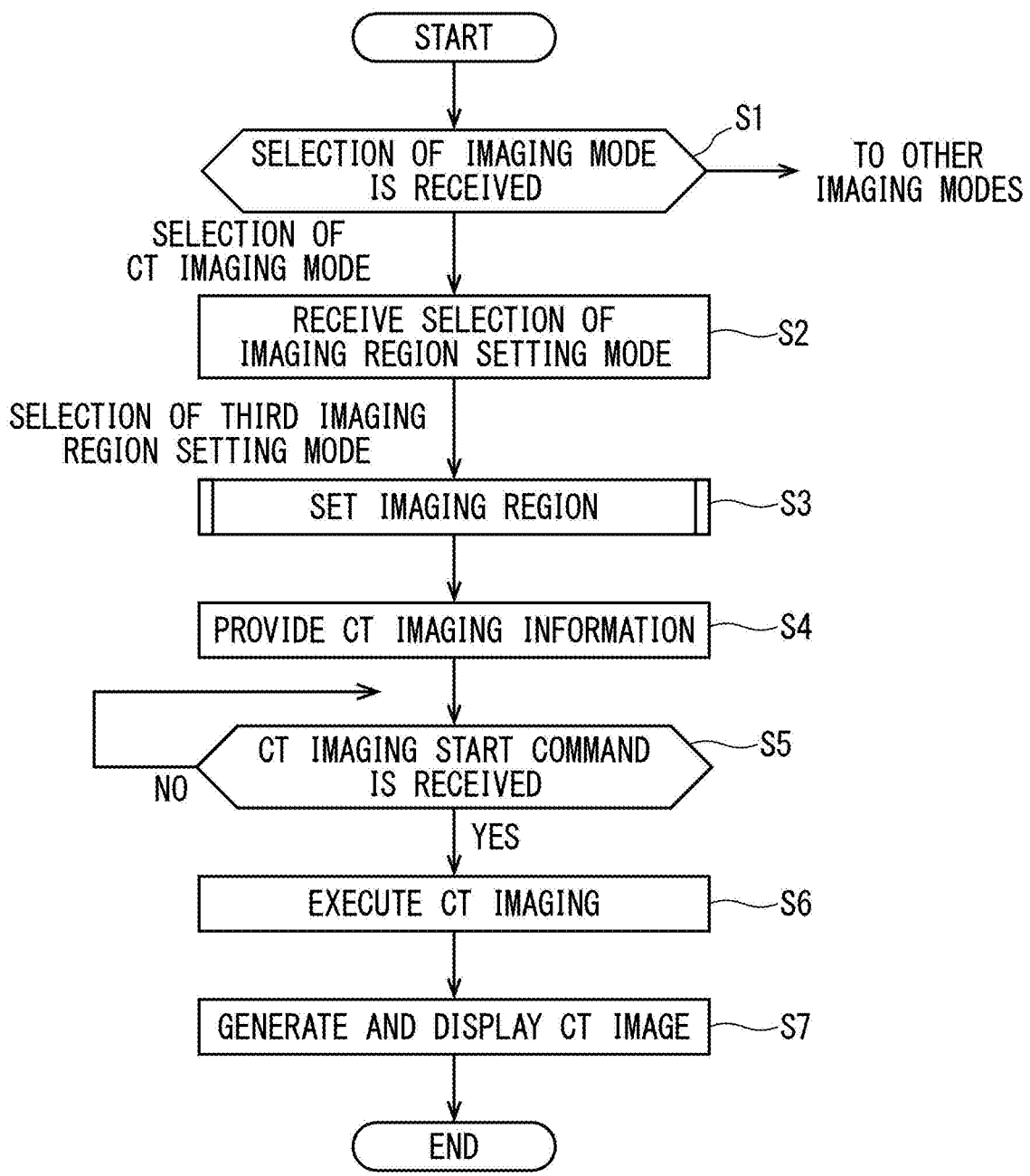
FIG. 5 is a flowchart illustrating operation of the X-ray imaging apparatus 1 of the first embodiment.
Figure 6:
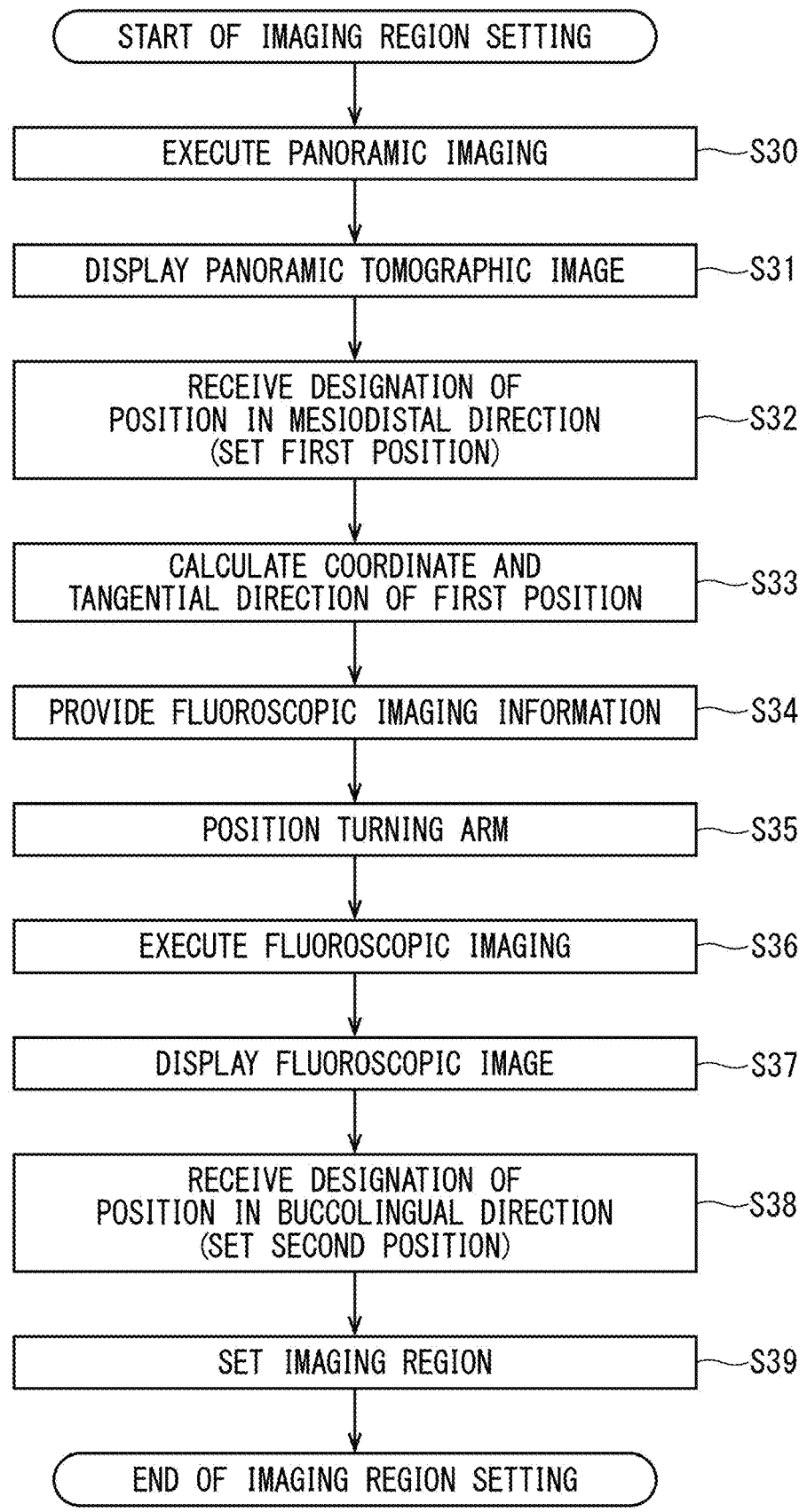
FIG. 6 is a flowchart illustrating operation of the X-ray imaging apparatus 1 of the first embodiment.

Operation of the X-ray imaging apparatus 1 will be described below. FIGS. 5 and 6 are flowcharts illustrating the operation of the X-ray imaging apparatus 1 of the first embodiment. Unless otherwise specified, the following operation of the X-ray imaging apparatus 1 is executed under the control of the main body controller 60 or the information processing main body 80 of the main body 2.

The selection of an imaging mode is received by the X-ray imaging apparatus 1 (step S1 in FIG. 5). The selection of the imaging mode can be received by the operation unit 86 of the information processing apparatus 8 or the operation displays 61, 62 of the main body 2. A fluoroscopic imaging mode executing the fluoroscopic imaging, a panorama imaging mode executing the panoramic imaging, and a CT imaging mode executing the CT imaging can be selected as the imaging mode. In the case that cephalogram imaging (head X-ray standard photograph) can be executed in the X-ray imaging apparatus 1, a mode executing cephalographic imaging can also be selected.

The case that the CT imaging mode is selected in step S1 will be described below. In the case that a mode other than the CT imaging mode is selected in step S1, although the description is omitted, the processing corresponding to the selected mode is executed.

When the CT imaging mode is selected, the X-ray imaging apparatus 1 receives the selection of the imaging region setting mode setting the imaging region (step S2 in FIG. 5). The imaging region setting mode includes a first imaging region setting mode in which the panoramic tomographic image is displayed on the display 85 to set the imaging region from the position designated by the manipulator on the panoramic tomographic image. A second imaging area setting mode in which two fluoroscopic images obtained by executing the fluoroscopic imaging from two directions are displayed on the display section 85 to set the imaging region from position designated by the manipulator on each fluoroscopic image is also included as another imaging region setting mode.

A third imaging region setting mode in which the panoramic tomographic image and the fluoroscopic image are used is included as still another imaging region setting mode. The flow of the third imaging region setting mode will be described in detail later with reference to FIG. 6.

When one mode is selected from the plurality of imaging region setting modes in step S2, the imaging region FOV of the CT imaging is set according to the selected mode (step S3 in FIG. 5). Then, the CT imaging information executing the CT imaging is provided from the information processing device 8 to the main body 2 (step S4 in FIG. 5). In particular, the CT imaging information providing unit 805 provides the CT imaging information to the main body controller 60. For example, the CT imaging information may include information about a coordinate position in the real space of the imaging region set in step S3. Various pieces of information can be included in the CT imaging information in addition to the information about the turning start position of the turning arm 30 and the information about the X-ray intensity (in particular, a voltage value or a current value supplied to the X-ray tube).

When the CT imaging information is provided from the information processing device 8 to the main body 2, the X-ray imaging device 1 receives a CT imaging start instruction (step S5 in FIG. 5). The CT imaging start command is a command that is a trigger starting the CT imaging in the main body 2. The manipulator can provide the CT imaging start command to the main body 2 by operating the imaging start switch 65a of the switch 65 or another operation unit (the operation displays 61, 62, the operation unit 86).

When the CT imaging start command is issued (YES in step S5), the main body 2 executes the CT imaging (step S6 in FIG. 5). In particular, the main body 2 moves the turning arm 30 to the turning start position according to the CT imaging information provided in step S4. Then, the main body 2 starts the turning of the turning arm 30, and irradiates the imaging region of the head M10 set in step S3 with the X-ray cone beam. The X-ray cone beam is an X-ray beam formed into a shape spreading in, for example, a quadrangular pyramid shape by the beam shaping mechanism 13. During the turning of the turning arm 30, the main body 2 detects the X-ray cone beam emitted from the X-ray generator 11 using the X-ray detector 21, thereby taking an image signal obtained at a predetermined frame rate, namely, the projection data in the storage. The main unit 2 transmits the taken projection data to the information processing main body 80. Consequently, the projection data is accumulated in the information processing device 8.

Subsequently, CT image generation processing and CT image display processing are executed in the information processing apparatus 8 (step S7 in FIG. 5). In particular, the image processor 806 of the information processing main body 80 generates a slice image that is the CT image by reconstructing the projection data acquired by the CT imaging in step S6. The information processing main body 80 displays the generated slice image on the display 85. A condition setting related to the reconstruction by the manipulator (a type of a reconstruction function, a setting of sectional thickness) may be accepted during the reconstruction processing. The selection of the slice image displayed on the display 85 by the manipulator may be receivable during the display processing.

The setting of the imaging area FOV in step S3 will be described in detail below with reference to FIG. 6. FIG. 6 is a flowchart illustrating the third imaging region setting mode in which the imaging region FOV is set using the panoramic tomographic image and the fluoroscopic image.

In the third imaging region setting mode, the main body 2 executes the panoramic imaging on the head M10 (step S30 in FIG. 6). Specifically, the main body controller 60 of the main body 2 controls the X-ray generating unit 10, the X-ray detecting unit 20, the turning motor 32, and the XY table 34 to execute the panoramic imaging in which a panoramic sectional image of the jaw of the head M10 is acquired. In the panoramic imaging, the X-ray beam emitted from the X-ray generator 11 is shaped into the X-ray narrow beam extending in the vertical direction by the beam shaping mechanism 13. The turning arm 30 moves along a locus for the panoramic imaging, which allows the curved surface corresponding to the dental arch to be irradiated with the X-ray narrow beam such that the X-ray narrow beam traces the curved surface from one end to the other end of the left and right sides. One panoramic tomographic image PI1 is generated by connecting the rectangular projection images obtained in this way. The panoramic tomographic image PI1 generated in this way is displayed on the display 85 (step S31 in FIG. 6). In this way, the main body controller 60 of the main body 2 is an example of the panoramic imaging execution unit that executes the panoramic imaging.

Figure 7:
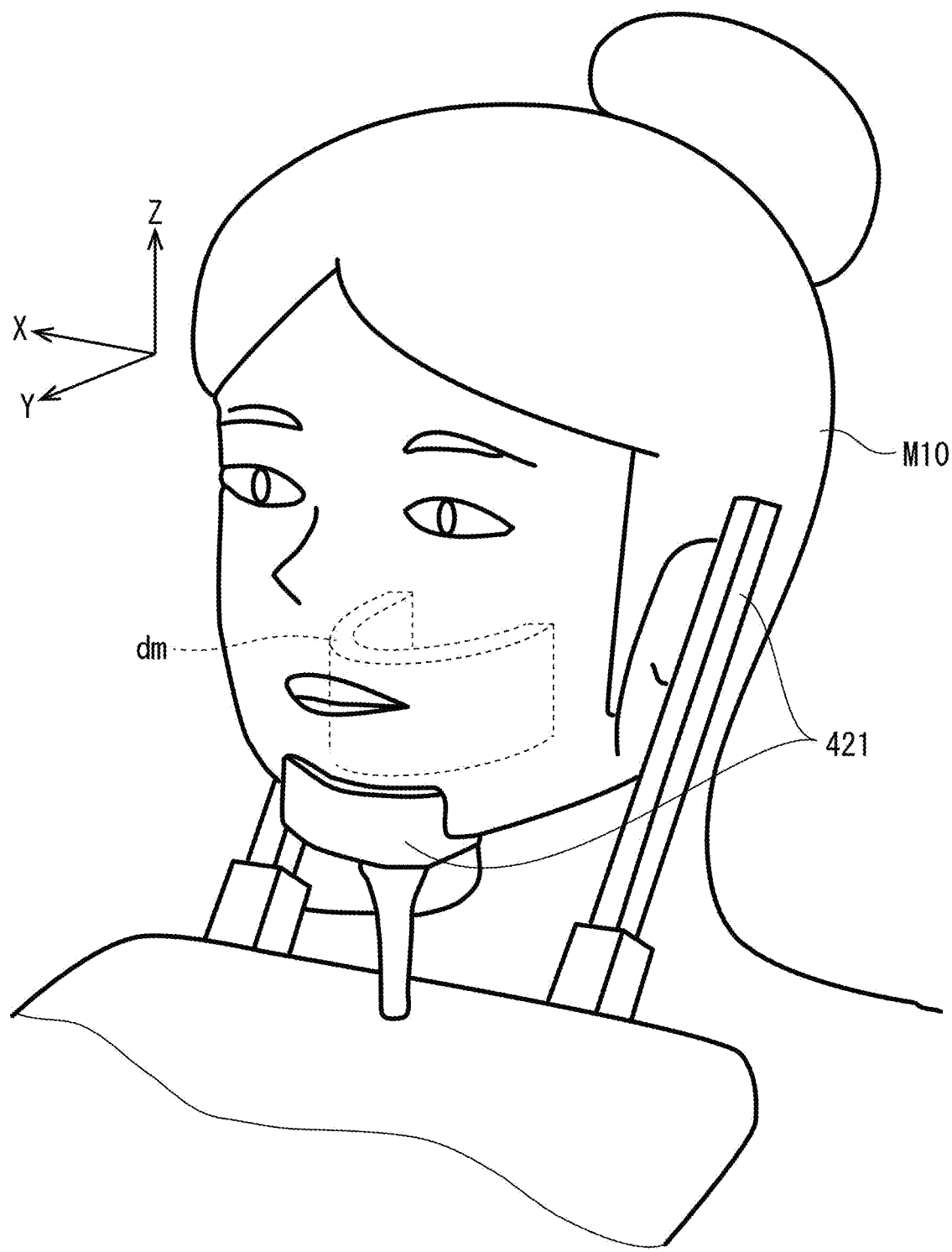
FIG. 7 is a schematic perspective view illustrating a head M10 held by a subject holder 421.

FIG. 7 is a schematic perspective view illustrating the head M10 held by the subject holder 421. As illustrated in FIG. 7, the panoramic tomographic image of the curved section along the dental arch model dm is acquired while the jaw of the head M10 is placed on the tin rest of the subject holder 421. The dental arch model means a virtual three-dimensional shape along the dental arch of a human body that is a statistic standard. In this case, the dental arch model means a virtual imaging object (curved section), which has a horseshoe shape in planar view and has a predetermined thickness corresponding to a panoramic section. The panoramic imaging is executed on a portion in which the dental arch model dm exists.

The dental arch model dm occupies a fixed position with respect to the subject holder 421 in a real space (three-dimensional space). The position of the curved section indicated by the dental arch model dm is specified in the real space, so that the position (standard position) of the dental arch model is specified as coordinate information about a three-dimensional coordinate. The number of dental arch models dm is not limited to one. For example, a dental arch model dm corresponding to each of sexuality and an age group, such as an adult (an adult male or an adult female), a child, and an old man, may be prepared in advance. The dental arch model dm suitable for the head M10 may be selected from the plurality of dental arch models dm. Information about the dental arch model dm may readably be stored in the storage such as the hard disk 84.

Figure 8:
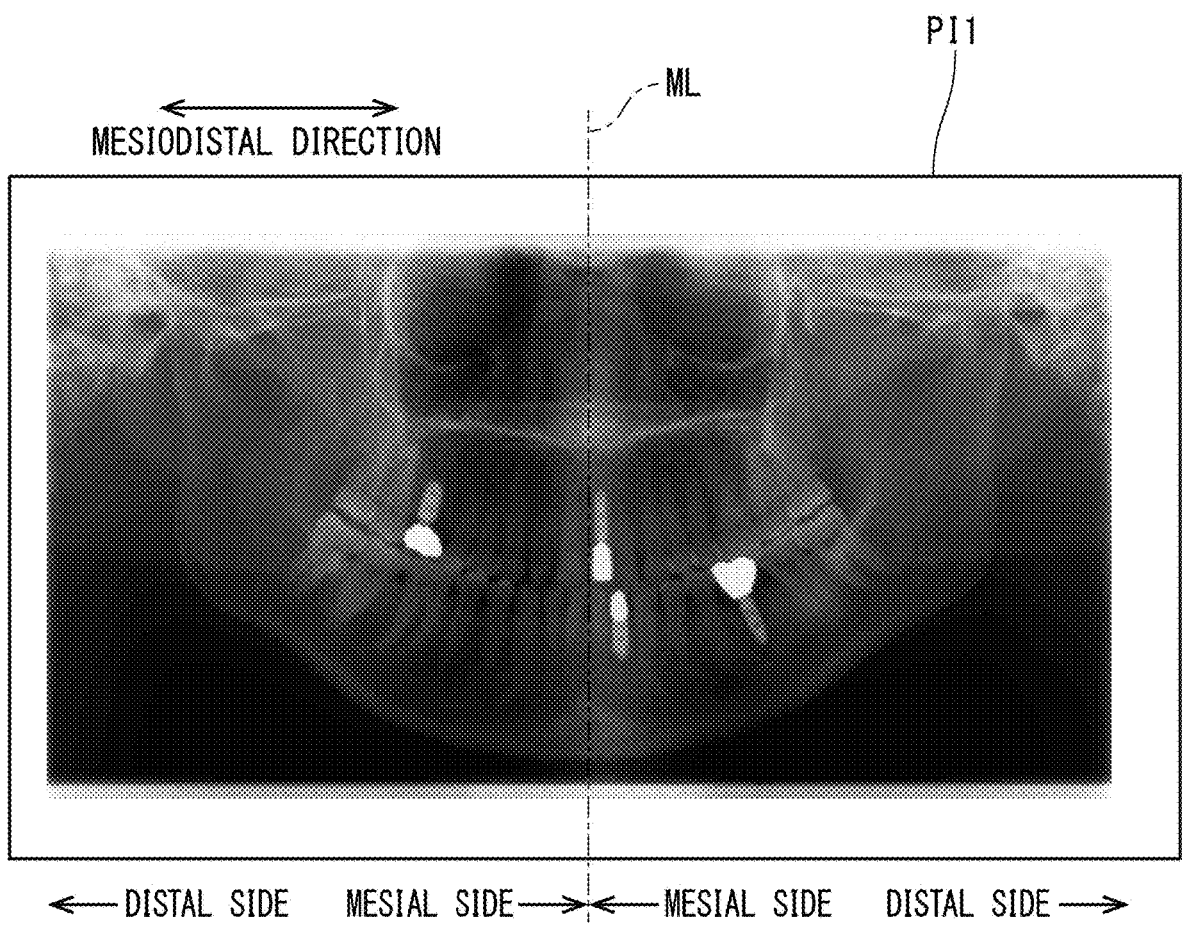
FIG. 8 is a view illustrating an example of a panoramic tomographic image PI1.

FIG. 8 is a view illustrating an example of the panoramic tomographic image PI1. As illustrated in FIG. 8, the panoramic tomographic image PI1 is an image in which the curved section indicated by the horseshoe-shaped dental arch model dm is linearly developed in the mesiodistal direction, so that an entire tooth row can be understood at a time. As illustrated in FIG. 8, the side close to a median line ML is a mesial side, and the side away from the median line ML is a distal side. The mesiodistal direction means a direction orthogonal to the median line, and a direction along the dental arch.

Referring to FIG. 6, when the panoramic tomographic image is displayed on the display 85 in step S31, the information processing apparatus 8 receives the designation of the first position Pos1 that is the position in the mesiodistal direction in order to set the position of the imaging region FOV (step S32 in FIG. 6).

Figure 9:
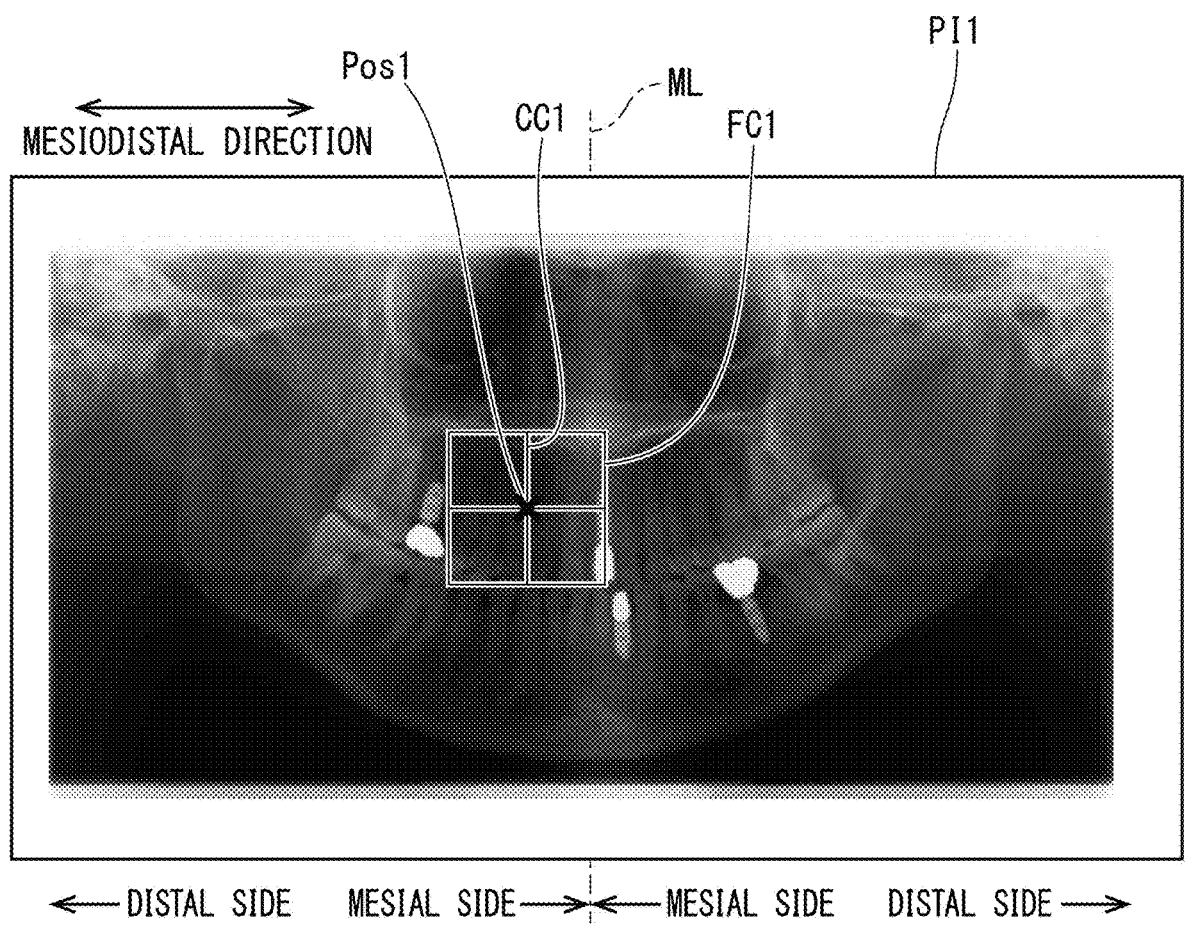
FIG. 9 is a schematic diagram illustrating a state in which a first position Pos1 in a mesiodistal direction is set on the panoramic tomographic image PI1.

FIG. 9 is a schematic diagram illustrating a state in which the first position Pos1 in the mesiodistal direction is set on the panoramic tomographic image PI1. In step S32, as illustrated in FIG. 9, the first position setting unit 801 receives the operation to designate the position the first position Pos1) in the mesiodistal direction while the panoramic tomographic image PI1 is displayed on the display 85. In the example of FIG. 9, a position designating cursor CC1 having a cross shape is displayed on the panoramic tomographic image PI1. The position designating cursor CC1 is constructed with two lines orthogonal to each other, and an intersection point of the lines is a portion in which the first position Pos1 is pointed. The manipulator operates the operation unit 86, which allows the position designating cursor CC1 to be moved to any position in the panoramic tomographic image PI1. After moving the position designating cursor CC1 to a desired region of interest (ROI), the manipulator performs a predetermined designation operation (such as a mouse click operation). Consequently, the first position setting unit 801 sets the position of the position designating cursor CC1 in the panoramic tomographic image PI1 to the first position Pos1 that is the position in the mesiodistal direction. The designation of the first position Pos1 of the position designating cursor CC1 also serves as the designation in the Z direction, such as the designation of upper jaw teeth, lower jaw teeth, a tooth crown, and a tooth root.

In the example of FIG. 9, the first position setting unit 801 displays a rectangular frame cursor FC1 that moves together with the position designating cursor CC1. Strictly speaking, the first position setting unit 801 issues a display command. The frame cursor FC1 schematically indicates a boundary (outer edge) of the imaging region FOV. The region inside the frame cursor FC1 is the imaging region FOV. That is, the frame cursor FC1 is a range index indicating a range of the imaging region FOV. The manipulator can move the position designating cursor CC1 and the frame cursor FC1 such that the region of interest falls within the frame cursor FC1. A size of the frame cursor FC1 may be changed according to a size of the region of interest.

The panoramic tomographic image PI1 displayed on the display 85 may not be acquired by the X-ray imaging apparatus 1, but may be acquired by another X-ray imaging apparatus. However, in this case, in order to specify the coordinate of the first position Pos1 in the real space, it is necessary to specify a positional relationship between the position of the dental arch model dm in another X-ray imaging apparatus that acquires the panoramic tomographic image PI1 and the position of the dental arch model dm in the X-ray imaging apparatus 1. Even if the panoramic imaging is not necessarily executed after the CT imaging mode is selected, the panoramic image acquired in the past by the X-ray imaging apparatus 1 may be saved and used by calling the panoramic image.

Referring to FIG. 6, when the first position Pos1 that is the position in the mesiodistal direction is set, the fluoroscopic imaging information providing unit 802 specifies the coordinates of the real space the first position Pos1 on the curved section corresponding to the panoramic tomographic image and the tangential direction TLD1 at the first position Pos1 (step S33 in FIG. 6). That is, by specifying the position on the panoramic tomographic image PI1, the XYZ coordinates of the first position Pos1 on the dental arch model dm are specified, and the tangential direction TLD1 is specified.

Figure 10:
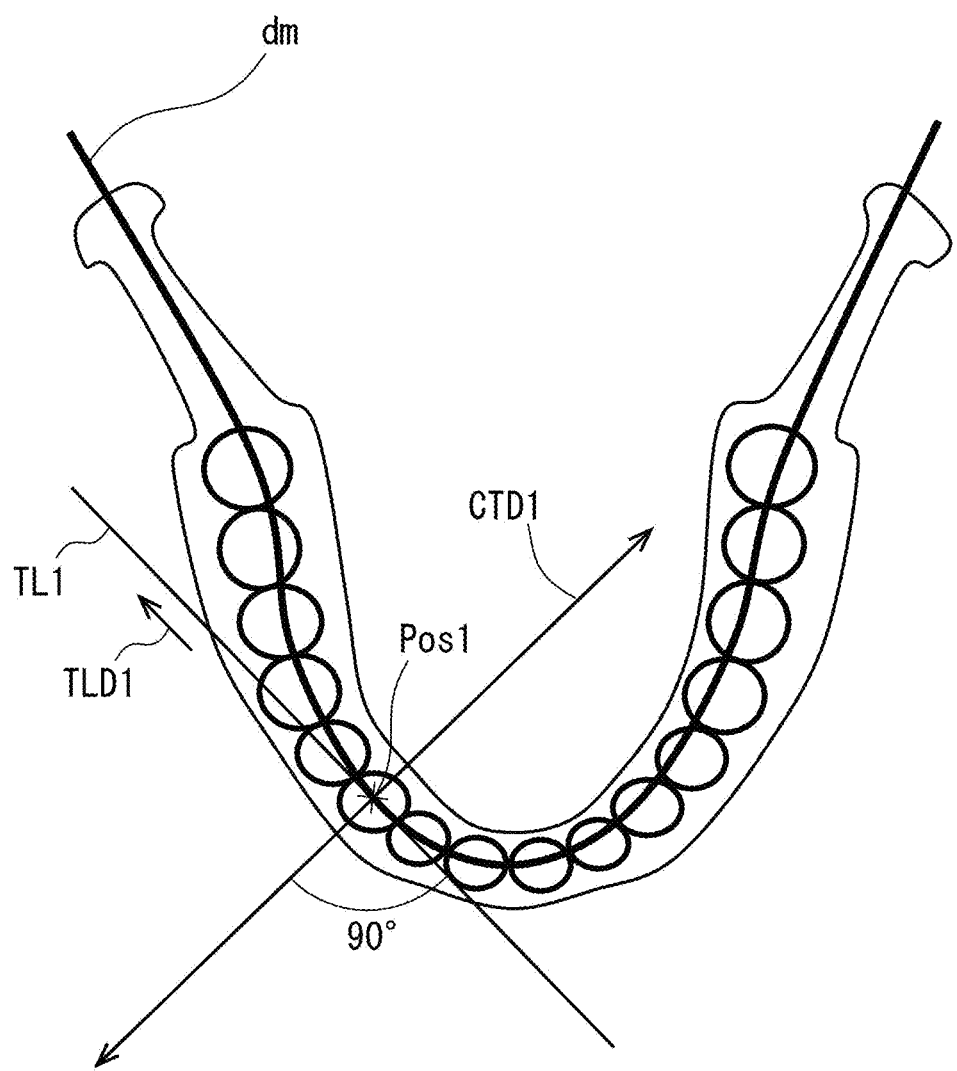
FIG. 10 is a plan view schematically illustrating a lower jaw of the head M10 and a dental arch model dm when the lower jaw of the head M10 and the dental arch model dm are viewed from a +Z side.

The tangential direction TLD1 will be described. FIG. 10 is a plan view schematically illustrating the lower jaw of the head M10 and the dental arch model dm when the lower jaw of the head M10 and the dental arch model dm are viewed from the +Z side. As illustrated in FIG. 10, when the first position Pos1 on the dental arch model dm that is the curved sectional plane is set by the first position setting unit 801, the fluoroscopic imaging information providing unit 802 obtains the coordinate of the first position Pos1, and calculates a vector of the tangential direction TLD1 that is a direction in which a tangential line TL1 passing through the coordinate of the first position Pos1 extends. Information on the calculated tangential direction TLD1 is stored in the storage such as the RAM 83. The tangential direction TLD1 for each position of the dental arch model dm may previously be fixed and tabulated such that the table may appropriately be read.

Returning to FIG. 6, when the coordinates and the tangential direction information of the first position Pos1 are calculated in step S33, these pieces of information are provided to the main body 2 as fluoroscopic imaging information (step S34 in FIG. 6). The fluoroscopic imaging information is a condition that executes the fluoroscopic imaging, and includes pieces of information such as the irradiation direction (an orientation of the central axis of the X-ray beam) of the X-ray beam emitted from the X-ray generating unit 10 and the imaging position (the position of a point on the real space through which the central axis of the X-ray beam passes) of the X-ray beam. Upon receiving the fluoroscopic imaging information, the main body controller 60 positions the turning arm (step S35 in FIG. 6). The main body controller 60 executes the fluoroscopic imaging in which the imaging region is irradiated with the X-ray beam while the head M10 is fixed to the subject holder 421 (step S36 in FIG. 6). When the fluoroscopic imaging is completed, the acquired fluoroscopic image is displayed on the display 85 (step S37 in FIG. 6).

Figure 11:
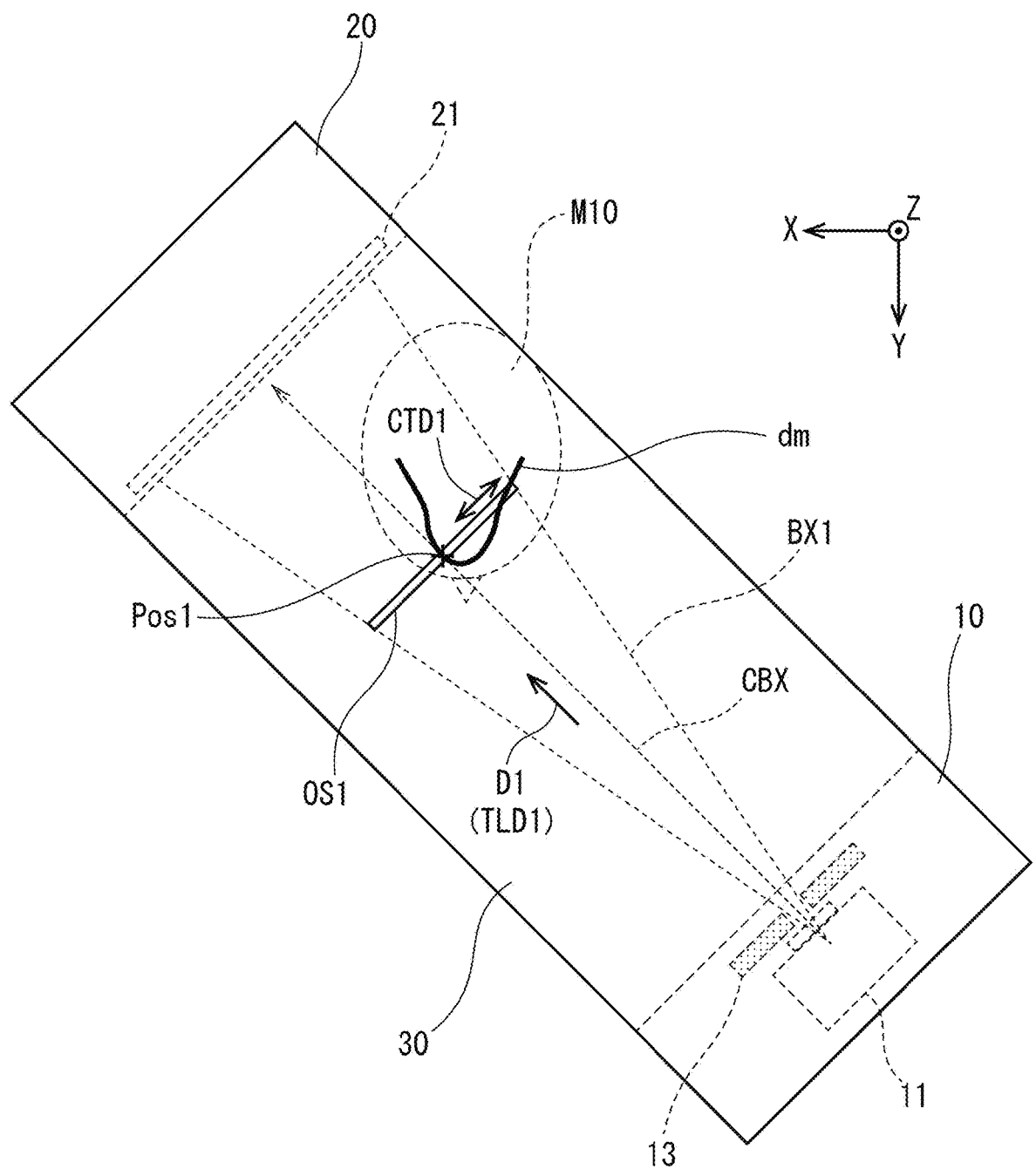
FIG. 11 is a schematic plan view illustrating a turning arm 30 of the main body 2 that executes fluoroscopic imaging viewed from the +Z side.

FIG. 11 is a schematic plan view illustrating a turning arm 30 of the main body 2 that executes fluoroscopic imaging viewed from the +Z side. As illustrated in FIG. 11, when the fluoroscopic imaging information is provided to the main body 2, the main body controller 60 controls the positioning of the turning arm 30 such that the irradiation direction (the orientation of a central axis CBX) of an X-ray beam BX1 emitted from the X-ray generating unit 10 is matched with the tangential direction TLD1, and such that the central axis CBX of the X-ray beam BX1 passes through the coordinate of the first position Pos1. Specifically, an angle in a horizontal plane of the turning arm 30 is adjusted by driving the turning motor 32, whereby the irradiation direction of the X-ray beam BX1 is matched with the tangential direction TLD1. The horizontal position and the vertical position of the turning arm 30 are adjusted by driving the XY table 34 and the elevation drive unit 43. The driving of the lift driving unit 44 may be accompanied by the driving of the lift driving unit 43. For example, this is synchronous driving with the identical displacement amount as described above. Consequently, the central axis CBX of the X-ray beam BX1 is positioned so as to pass through the first position Pos1.

When the positioning of the turning arm 30 is completed in this manner, the X-ray beam BX1 shaped by the beam shaping mechanism 13 is emitted from the X-ray generating unit 10, and the head M10 held by the subject holder 421 is irradiated with the X-ray beam BX1. Consequently, the X-ray beam BX1, which passes through the first position Pos1 and is transmitted through an orthogonal plane OS1 orthogonal to the irradiation direction (the direction parallel to the tangential direction TLD1), is detected the X-ray detector 21 as illustrated in FIG. 11.

An imaging width (a horizontal width) of the X-ray beam BX1 during the fluoroscopic imaging is not particularly limited. However, for example, when the image diagnosis is assumed in the dental examination, the region of interest often exists around the tooth. Consequently, the imaging width of the X-ray beam BX1 is preferably set to a size including a periphery of about 2 cm of the first position Pos1. In this manner, the exposure dose of the examinee can be reduced by reducing the imaging width of the X-ray beam BX1.

Returning to FIG. 6, when the fluoroscopic image SI1 is displayed on the display 85 in step S37, the information processing device 8 receives the designation of the second position Pos2 that is the position in the buccolingual direction in order to set the imaging region FOV (step S38 in FIG. 6). The designation reception of the second position Pos2 will specifically be described with reference to FIG. 12.

Figure 12:
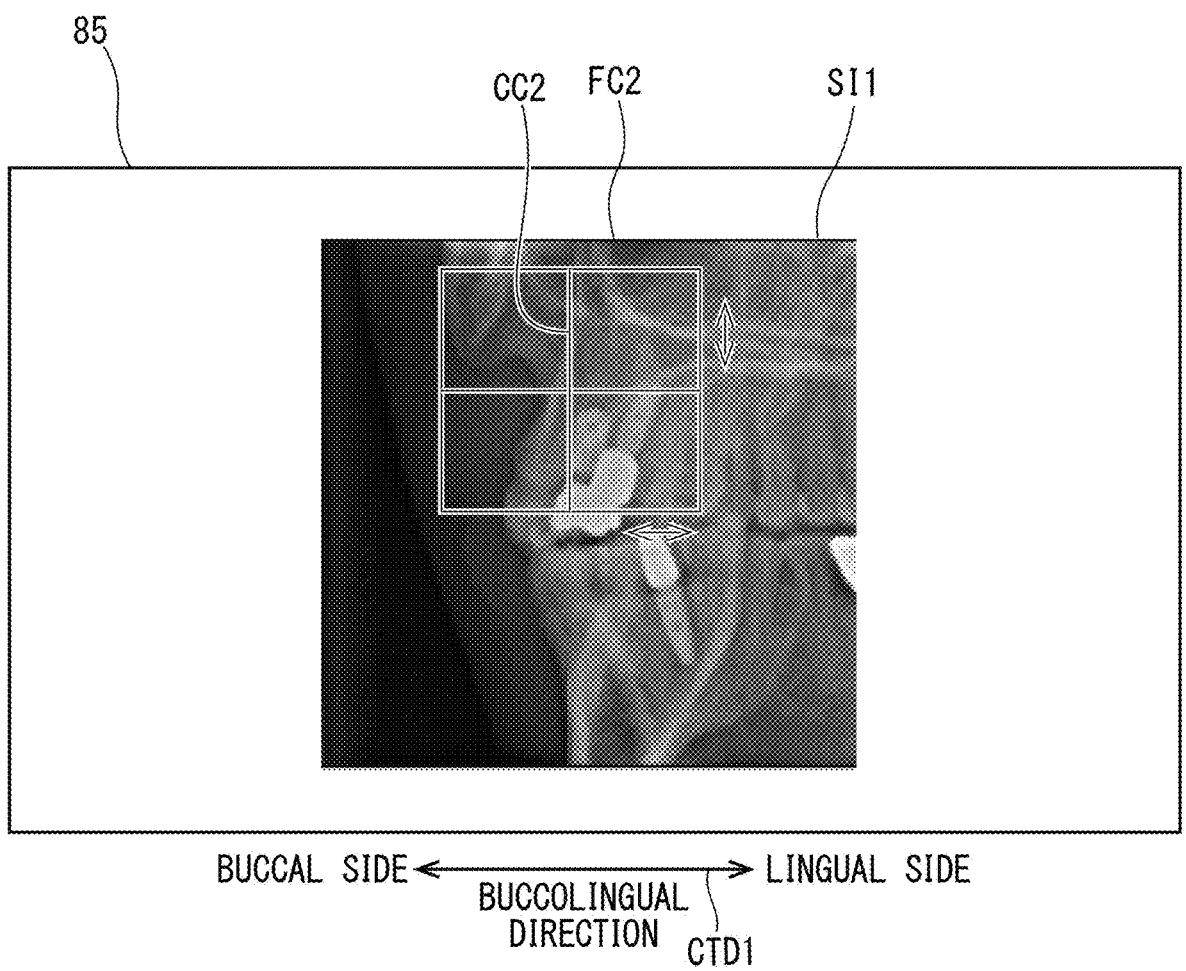
FIG. 12 is a view illustrating a display example of a fluoroscopic image SI1.

FIG. 12 is a view illustrating a display example of a fluoroscopic image SI1. In the example of FIG. 12, in order to set the second position Pos2 of the buccolingual direction CTD1 in FIG. 15, a cross-shaped position designating cursor CC2 is displayed on the fluoroscopic image SI1. Similarly to the position specifying cursor CC1, the position designating cursor CC2 is also constructed with two lines orthogonal to each other, and the intersection point of the lines is a portion in which the second position Pos2 is pointed. The manipulator can move the position designating cursor CC2 to any position in the fluoroscopic image SI1 by operating the operation unit 86. After moving the position designating cursor CC2 to the desired region of interest (ROI), the manipulator performs a predetermined designation operation (such as a mouse click operation). Consequently, the second position setting unit 803 sets the position of the position designating cursor CC2 in the fluoroscopic image SI1 to the second position Pos2 that is the position in the buccolingual direction.

In the example of FIG. 12, the second position setting unit 803 displays a rectangular frame cursor FC2 that moves together with the position designating cursor CC2. Strictly speaking, the second position setting unit 803 issues a display command. The frame cursor FC2 is a range index schematically indicating the boundary (outer edge) of the imaging region FOV. That is, the region inside this frame cursor FC2 is finally set to the imaging region FOV. Consequently, the manipulator can suitably set the imaging region FOV by including the region of interest in the frame cursor FC2.

The initial display position before the operation to designate the position designating cursor CC2 and the second position Pos2 of the frame cursor FC2 may be displayed in conformity with the position of the first position Pos1 on the dental arch model dm.

In the fluoroscopic image SI1 of FIG. 12, the perpendicular direction corresponds to the vertical direction (Z direction) of the real space. Thus, the second position Pos2 set by reading the position on the image of the position designating cursor CC2 includes not only the positional information about the buccolingual direction CTD1 in the real space, but also the positional information about the vertical direction in the real space.

That is, by designating the position on the fluoroscopic image SI1, the XYZ coordinate of the second position Pos2 in the real space is specified, and the position of the imaging region FOV is specified.

When the coordinate information is provided to the main body 2, the main body controller 60 controls the positioning of the turning arm 30 such that the imaging region FOV in which the position is specified is irradiated with the X-ray beam BX1, specifically, the X-ray cone beam BX1 while the X-ray beam BX1 turns. Specifically, the horizontal position and the vertical position of the turning arm 30 are adjusted by driving the XY table 34 and the elevation drive unit 43.

The driving of the lift driving unit 44 may be accompanied by the driving of the lift driving unit 43. For example, this is synchronous driving with the identical displacement amount as described above. At this point, the control is preferably performed such that the turning centers of the X-ray generator 11 and the X-ray detector 21 are located at the center of the imaging region FOV viewed from the Z direction. More preferably, the irradiation central axis of the X-ray cone beam BX1 is controlled so as to always pass through the second position Pos2 during the CT imaging. The position designating cursor CC2 may be movable to any position in the fluoroscopic image SI1, and configured such that the position of the position designating cursor CC2 can be changed only in the buccolingual direction CTD1 while the position in the Z direction is kept constant.

Figure 13:
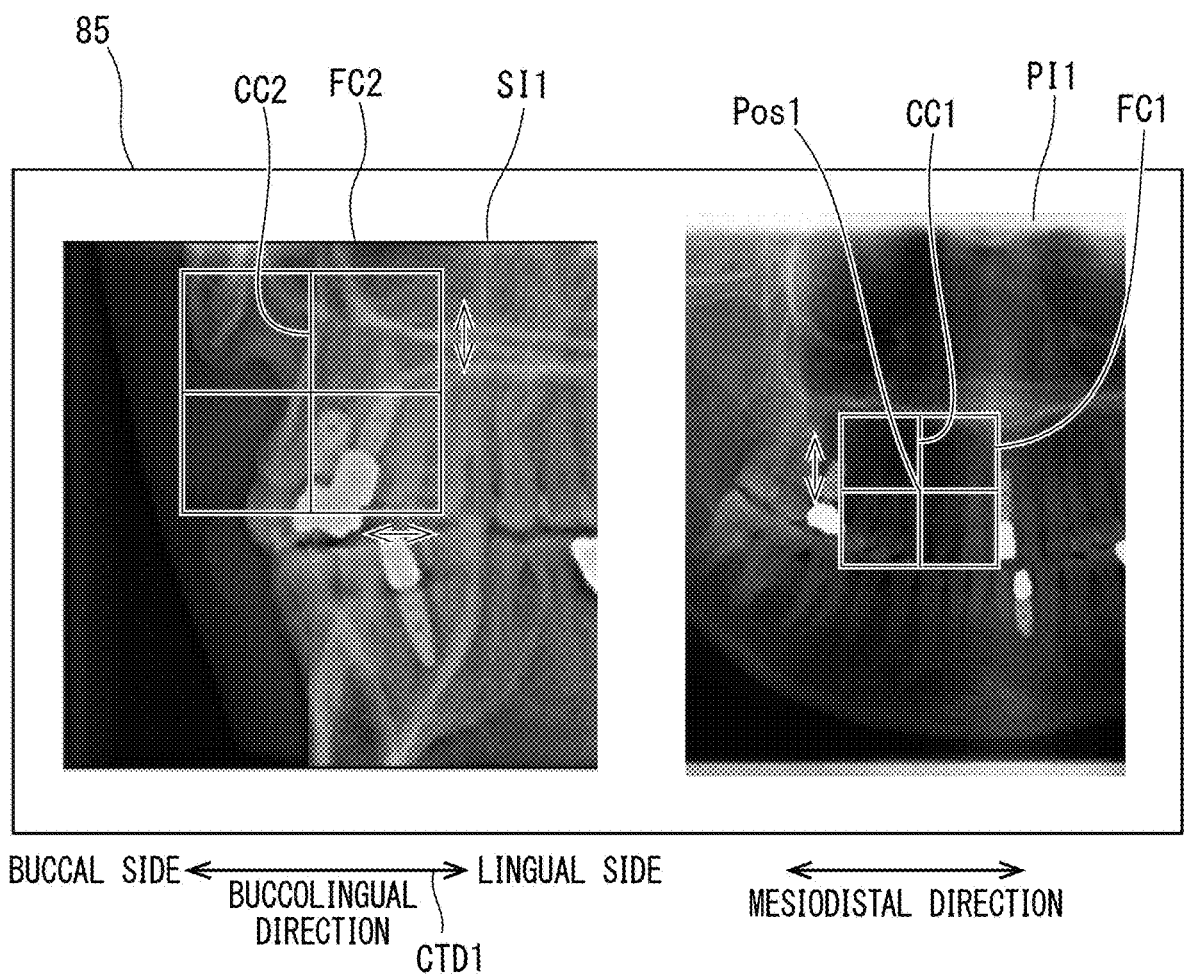
FIG. 13 is a view illustrating another display example of the fluoroscopic image SI1.

FIG. 13 is a view illustrating another display example of the fluoroscopic image SI1 in the buccolingual direction CTD1 of FIG. 15. In this display example, in setting the second position Pos2, the panoramic tomographic image PI1 and the fluoroscopic image SI1 are displayed in parallel on the display 85. The fluoroscopic image SI1 in the buccolingual direction CTD1 is displayed on the left of the screen of the display 85, and the panoramic tomographic image PI1 is displayed on the right of the screen. The fluoroscopic image SI1 and the panorama tomographic image PI1 are not necessarily displayed side by side on the screen, but the fluoroscopic image SI1 and the panorama tomographic image PI1 may vertically be displayed side by side.

In this example, in the panoramic tomographic image PI1 of FIGS. 8 and 9, a partial image obtained by cutting out a peripheral portion of the previously-set first position Pos1 is displayed in parallel to the fluoroscopic image SI1. In this case, the display of an unnecessary region in the panoramic tomographic image PI1 is omitted, so that the display region of the display 85 can effectively and widely be used. However, the entire panoramic tomographic image PI1 is not prevented from being displayed together with the fluoroscopic image SI1.

In the display example of FIG. 13, when the position designating cursor CC2 on the fluoroscopic image SI1 is moved up and down, the position designating cursor CC1 on the panoramic tomographic image PI1 is also moved up and down in conjunction with the position designating cursor CC2. However, even if the position designating cursor CC2 is moved in the horizontal direction (buccolingual direction), the position designating cursor CC1 is not moved. This is because the buccolingual direction corresponds to the direction perpendicular to the image plane of the panoramic tomographic image.

By displaying the fluoroscopic image SI1 and the panoramic tomographic image PI1 in this manner, the manipulator can check the structure around the region of interest from the two directions. Consequently, the imaging region FOV can be set more suitably as compared with the case that only the fluoroscopic image SI1 is displayed.

Figure 14:
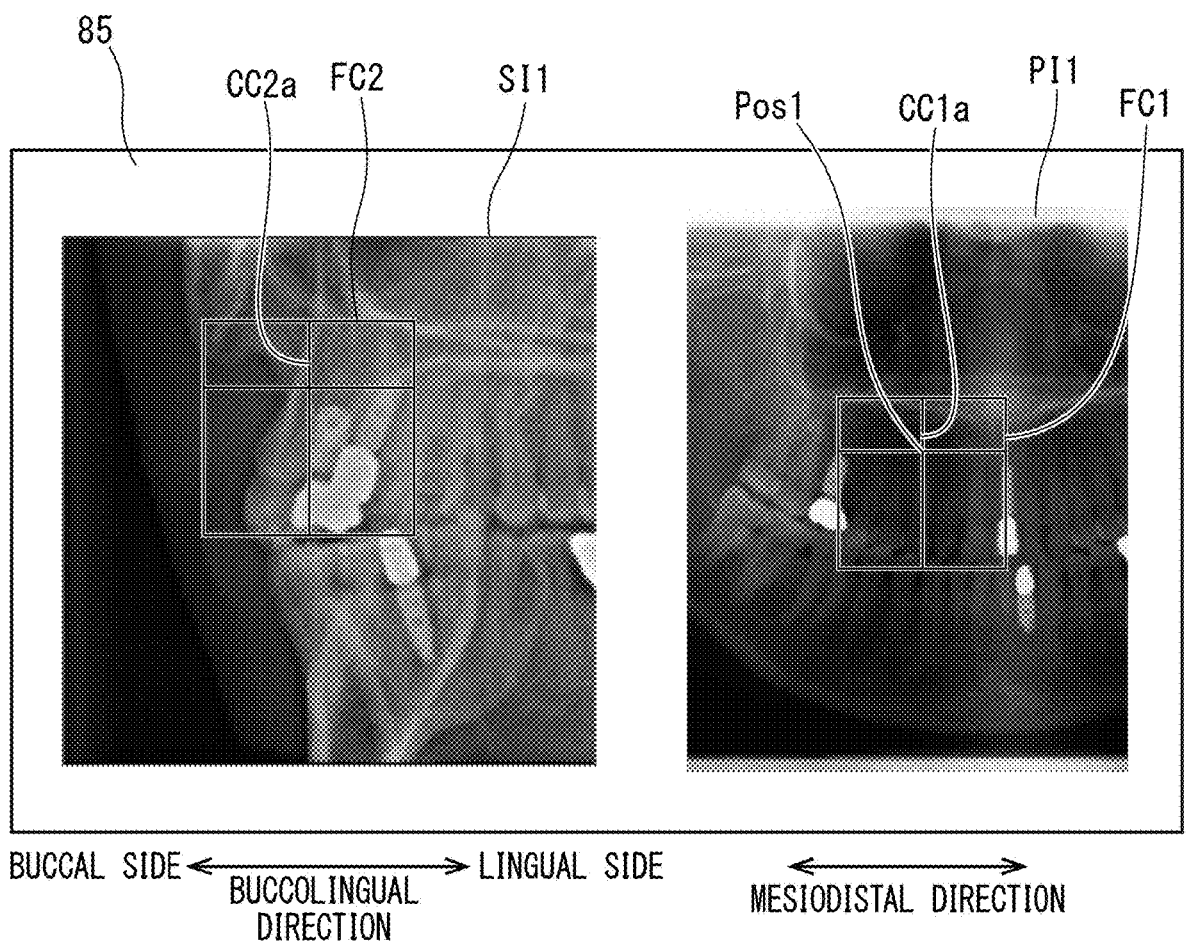
FIG. 14 is a view illustrating still another display example of the fluoroscopic image SI1.

FIG. 14 is a diagram illustrating still another display example of the fluoroscopic image SI1 in the buccolingual direction CTD1 of FIG. 15. In this display example, similarly to the display example in FIG. 13, in setting the second position Pos2, the panoramic tomographic image PI1 is displayed on the display 85 in parallel to the fluoroscopic image SI1. The intersection point of a position designating cursor CC2a pointing to the second position Pos2 is vertically biased with respect to the frame cursor FC2. More specifically, for example, when being disposed in the vicinity of the tooth root of the upper jaw in the fluoroscopic image SI1, the intersection point of the position designating cursor CC2a is displayed so as to be closer to the upper side in the vertical direction with respect to the frame cursor FC2. On the other hand, although not illustrated, when being disposed in the vicinity of the tooth root of the lower jaw of the fluoroscopic image SI1, the intersection point of the position designating cursor CC2a is displayed so as to be closer to the lower side in the vertical direction with respect to the frame cursor FC2.

This is because the intersection point of the position designating cursor CC2a indicates the position of a main line (the X-ray having the highest intensity) of the X-ray beam. That is, in the case that the second position Pos2 is designated by the position designating cursor CC2a, the position of the intersection point is irradiated with the main line of the X-ray beam. For example, in the case that the periphery of an apical portion of the upper jaw tooth is taken as the imaging object, the tooth is included in the imaging region by including the tooth in the frame cursor FC2. The position designating cursor CC2a is displayed while biased upward in the frame cursor FC2, so that the position biased upward in the imaging region is irradiated with the main line of the X-ray beam. Consequently, the periphery of the apical portion located on the upper side of the upper jaw tooth is irradiated with the main line, so that the periphery of the apical portion is satisfactorily imaged. Conversely, in the case that the periphery of the apical portion of the lower jaw tooth, the intersection point of the position designating cursor CC2a is displayed on the lower side of the frame cursor FC2, so that the slightly lower side of the center of the imaging region is irradiated with the main line of the X-ray beam while the lower jaw tooth is included in the imaging region. For this reason, the periphery of the apical portion on the lower side of the lower jaw tooth can satisfactorily be imaged.

The tooth constituting the tooth root in the region of interest can be included inside the frame cursor FC2 by biasing the intersection point of the position designating cursor CC2a. The entire tooth is easily included in the imaging region FOV, and therefore the observer of the CT image can more easily understand the structure of the entire tooth.

In setting the first position Pos1, the position designating cursor CC1a in FIG. 14 may be displayed on the panoramic tomographic image PI1. Similarly to the position designating cursor CC1 in FIG. 9, the position designating cursor CC1a is the portion in which the first position Pos1 is pointed by the intersection point of the two straight lines. For the position designating cursor CC1a, similarly to the position designating cursor CC2a, the intersection point of the position designating cursor CC1a may be biased upward or downward with respect to the frame cursor FC1 when the intersection point is disposed in the vicinity of the tooth root of the upper jaw or the lower jaw.

For example, in the case that an interest is focused on the vicinity of the tooth root of the upper jaw, the intersection point of the position designating cursor CC1a may be biased upward with respect to the frame cursor FC1, and the intersection point of the position designating cursor CC2a may be biased upward with respect to the frame cursor FC2. In the case that an interest is focused on the vicinity of the tooth root of the lower jaw, the intersection point of the position designating cursor CC1a may be biased downward with respect to the frame cursor FC1, and the intersection point of the position designating cursor CC2a may be biased downward with respect to the frame cursor FC2.

In this way, the intersection point of the position designating cursor CC1a may be displayed at the center of the frame cursor FC1 such that the intersection point of the position designating cursor CC2a is located at the center of the frame cursor FC2 or such that the intersection point of the position designating cursor CC2a is biased upward or downward with respect to the frame cursor FC2. The position of the beam shaping mechanism 13 with respect to the X-ray generator 11 may be changed according to the intersection point, or changed in synchronization with an operation to displace the intersection point.

Referring to FIG. 6, when the second position Pos2 is set in step S38, the information processing apparatus 8 sets the imaging region FOV based on the second position Pos2. Specifically, the imaging region setting unit 804 sets the region within a certain range centered on the second position Pos2 to the imaging region FOV.

FIG. 15 is a view illustrating a setting example of the imaging region FOV. In the example of FIG. 15, the second position Pos2, which is set by the second position setting unit 803 and designated by the manipulator, is separated from the first position Pos1 on the lingual side (inside) in the buccolingual direction CTD1 on the dental arch model dm. A substantially columnar region extending in parallel to the vertical direction (Z direction) is set to the imaging region FOV with the second position Pos2 as the imaging center.

When the imaging region FOV is set as described above, the CT imaging information providing unit 805 provides the main body 2 with the information about the imaging region FOV (for example, the positional information about the central axis RA1 of the imaging region FOV and a radius size) as described in step S4 of FIG. 5.

Consequently, in the main body 2, the CT imaging of the imaging region FOV is executed (step S6 in FIG. 5).

Effect

According to the X-ray imaging apparatus 1 of the first embodiment, the first position Pos1 can be designated on the panoramic tomographic image PI1 in which the plurality of teeth are observable while developed, so that the imaging region FOV of the CT imaging can suitably be positioned in the mesiodistal direction along the dental arch. The fluoroscopic imaging is executed with the tangential direction TLD1 of the first position Pos1 in the dental arch model dm (curved surface fault) as the irradiation direction (imaging direction D1), which allows the acquisition of the fluoroscopic image in the direction intersecting at the first position Pos1. The position in the direction intersecting the dental arch model dm, namely, the position in the buccolingual direction can be designated as the second position Pos2 by receiving the position designation on the fluoroscopic image. Consequently, the imaging region FOV can suitably be positioned in the buccolingual direction.

In the embodiment above, the imaging direction D1 of the fluoroscopic imaging is matched with the tangential direction TLD1. However, but the imaging direction D1 is not necessarily matched with the tangential direction TLD1. The imaging direction D1 may be a direction having at least the component of the tangential direction TLD1.

2. Second Embodiment

A second embodiment will be described below. In the following description, the element having the function similar to that of the already described element is denoted by the identical reference numeral or the reference numeral to which an alphabetical letter is added, and sometimes the detailed description will be omitted.

In the first embodiment, only one fluoroscopic image SI1 obtained by the imaging in one direction (tangential direction TLD1) is used to set the second position Pos2. However, the second position Pos2 in the buccolingual direction may be set using a plurality of fluoroscopic images obtained by the imaging from a plurality of directions.

Figure 16:
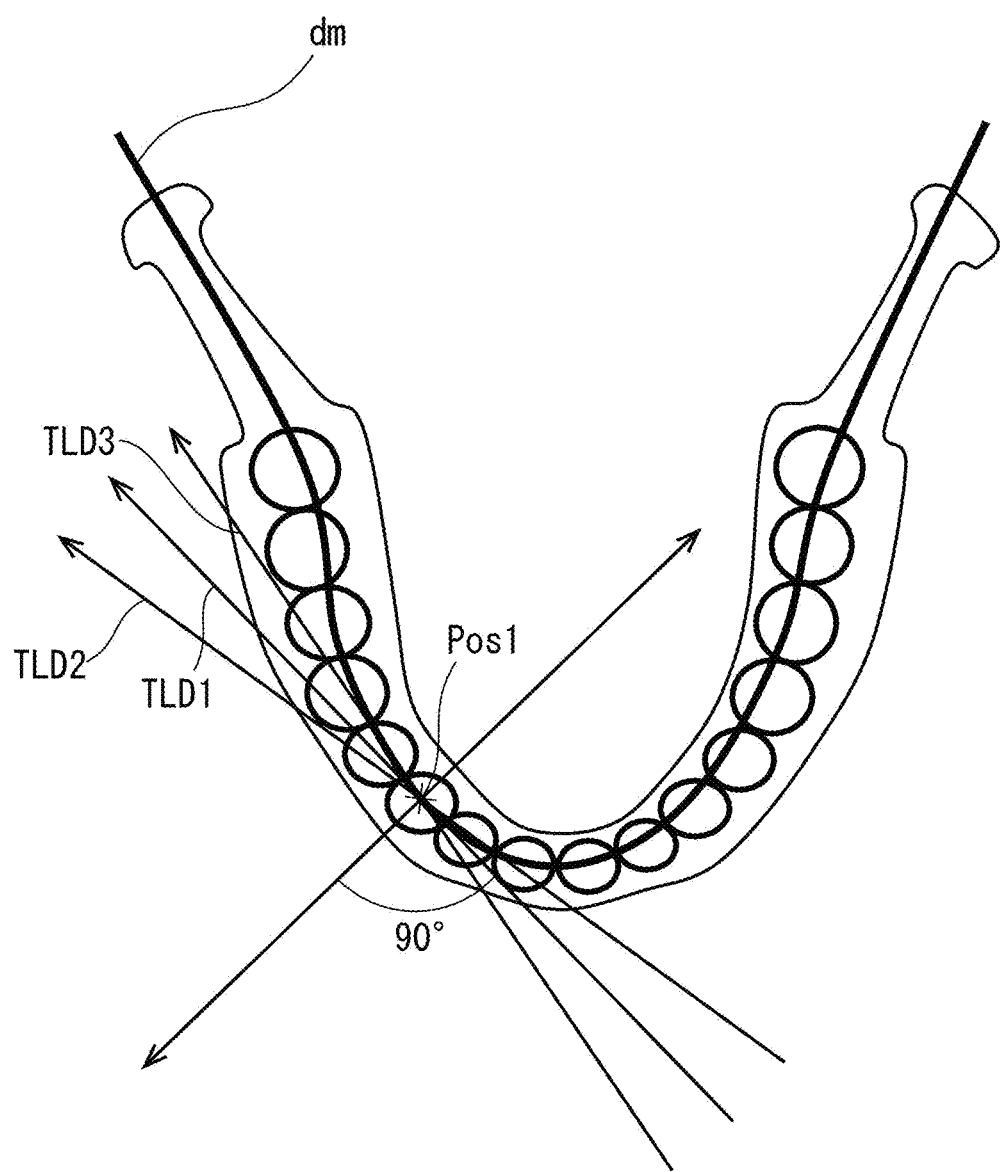
FIG. 16 is a plan view schematically illustrating the lower jaw of the head M10 and the dental arch model dm when the lower jaw of the head M10 and the dental arch model dm are viewed from the +Z side.
Figure 17:
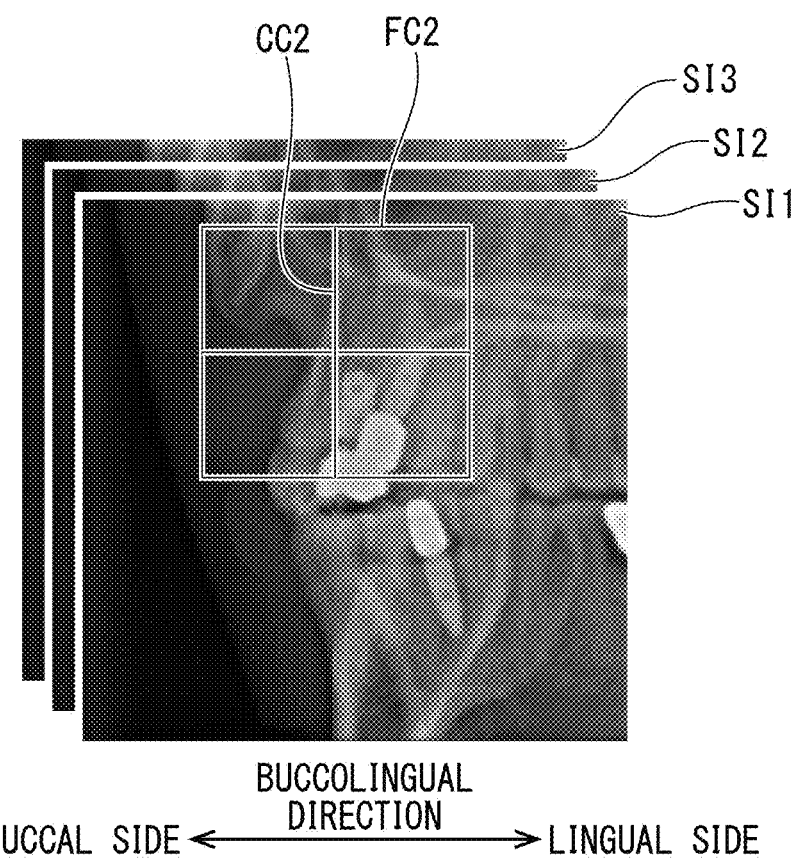
FIG. 17 is a view illustrating a plurality of fluoroscopic images SI1 to SI3.

FIG. 16 is a plan view schematically illustrating the lower jaw of the head M10 and the dental arch model dm when the lower jaw of the head M10 and the dental arch model dm are viewed from the +Z side. FIG. 17 is a view illustrating a plurality of fluoroscopic images SI1 to SI3. In this embodiment, as illustrated in FIG. 16, when the first position Pos1 is set, the tangential direction TLD1 at the first position Pos1 is specified similarly to the first embodiment. However, in this embodiment, two different directions TLD2, TLD3 having the component of the tangential direction TLD1 are further specified. In this case, the directions TLD2, TLD3 are directions in which the tangential direction TLD1 is inclined clockwise and counterclockwise in the horizontal plane by a predetermined angle (for example, 5° to 10°). The fluoroscopic imaging information providing unit 802 provides the imaging information in which the specified directions TLD1 to TLD3 are set to the fluoroscopic imaging directions to the main body 2. In the main body 2, as illustrated in FIG. 17, three fluoroscopic images SI1 to SI3 are acquired by irradiating the head M10 with the X-ray beams in the three directions TLD1 to TLD3.

For example, the fluoroscopic images SI1 to SI3 may simultaneously be arranged and displayed on the screen of the display 85 as display examples of the fluoroscopic images SI1 to SI3. The position designating cursor CC2 is displayed on each image, and the manipulator can designate the second position Pos2 on any image. Instead of simultaneously displaying the fluoroscopic images SI1 to SI3, the fluoroscopic images SI1 to SI3 may automatically or manually be switched and displayed one by one. For the display in which the fluoroscopic images SI1 to SI3 are automatically switched one by one, the fluoroscopic images SI1 to SI3 are continuously displayed like an animation. In this case, the manipulator may select a specific image by operating the operation unit 86 to stop the continuous display.

As described above, in this embodiment, the fluoroscopic imaging is executed from different angles, so that the manipulator can check the position of the region of interest from different angles. For example, in the fluoroscopic image viewed from one direction, sometimes the region of interest becomes obscure by overlapping with another structure. However, in the fluoroscopic image viewed from another direction, the overlap can be reduced. Consequently, the manipulator can designate the position (second position Pos2) in the buccolingual direction by selecting the image in which the region of interest is most easily checked. Thus, the imaging region FOV can suitably be set.

In the present embodiment, the case of performing fluoroscopic imaging in three directions has been described, but the fluoroscopic imaging may be executed in two directions or at least four directions.

In particular, the imaging of a small region (for example, the imaging region having a diameter of 3 cm and a height of 3 cm), which is the minimum necessary for the diagnosis, is executed in the recent dental X-ray CT imaging apparatus. X-ray exposure can be suppressed to the minimum by narrowing the imaging region in this way. Even in the case that the narrow region is imaged, the imaging region can properly be positioned by implementing certain implementations, so that the image diagnosis can satisfactorily be performed while the X-ray exposure is suppressed.

Although certain implementations have been described in detail, the above description is illustrative in all aspects, but the invention is not limited thereto. Innumerable modifications not illustrated can be envisaged without departing from the scope of the present invention. The respective configurations described in the above embodiments and modifications can appropriately be combined or omitted as long as they are inconsistent each other.

While certain implementations have been shown and described in detail, the foregoing description is in all aspects illustrative and not restrictive. It is therefore understood that numerous modifications and variations can be devised without departing from the scope of the invention.

What is claimed is:

1. A CT imaging apparatus comprising:
   an X-ray generator that emits an X-ray beam;
   an X-ray detector that detects said X-ray beam;
   a support that supports said X-ray generator and said X-ray detector such that said X-ray generator and said X-ray detector oppose each other;
   a turning motor that rotates said support around a rotation axis line located between said X-ray generator and said X-ray detector;
   a display that displays a panoramic tomographic image that is an image of a dental arch of a subject; and
   a processor configured to:
   receive an input of a designation operation to designate a position in a mesiodistal direction on said panoramic tomographic image displayed on said display, and set a first position on said panoramic tomographic image based on the designation operation;
   irradiate said subject with the X-ray beam along a fluoroscopic imaging direction having a tangential direction component at said first position on said panoramic tomographic image by controlling said X-ray generator, said X-ray detector, and said turning motor, and acquire a fluoroscopic image;
   receive an input of a designation operation to designate a position in a buccolingual direction on said fluoroscopic image displayed on said display, and set a second position based on the designation operation;
   set an imaging region of CT imaging based on said second position; and
   irradiate said imaging region set by said imaging region setting step with an X-ray cone beam by controlling said X-ray generator, said X-ray detector, and said turning motor, and execute said CT imaging.

2. The CT imaging apparatus according to claim 1, wherein said processor is further configured to receive designation to set said second position while said panoramic tomographic image and said fluoroscopic image are displayed in parallel on said display.

3. The CT imaging apparatus according to claim 2, wherein said processor is further configured to receive the designation to set said second position while a position index indicating said first position is displayed on said panoramic tomographic image displayed on said display.

4. The CT imaging apparatus according to claim 1, wherein said processor is further configured to display a range index indicating a range of said imaging region on said panoramic tomographic image displayed on said display.

5. The CT imaging apparatus according to claim 1, wherein said processor is further configured to display a range index indicating a range of said imaging region on said fluoroscopic image displayed on said display.

6. The CT imaging apparatus of claim 1, wherein the processor is further configured to execute panoramic imaging for acquiring said panoramic tomographic image.

7. A CT imaging method comprising:
   displaying a panoramic tomographic image of a dental arch of a subject on a display;
   receiving an input of a designation operation to designate a position in a mesiodistal direction on said panoramic tomographic image displayed on said display in said panoramic tomographic image displaying step, and setting a first position on said panoramic tomographic image based on the designation operation;
   acquiring a fluoroscopic image by irradiating said subject with an X-ray beam along a fluoroscopic imaging direction having a tangential direction component at said first position on said panoramic tomographic image set in said first position setting step;
   displaying said fluoroscopic image acquired in said fluoroscopic image acquiring step on said display;
   receiving an input of a designation operation to designate a position in a buccolingual direction on said fluoroscopic image displayed on said display in said fluoroscopic image displaying step, and setting a second position based on the designation operation;
   setting an imaging region of CT imaging based on said second position set in said second position setting step; and
   executing said CT imaging by irradiating said imaging region set in said imaging region setting step with an X-ray cone beam.

8. The CT imaging method according to claim 7, wherein said second position setting step receives a designation to set said second position while said panoramic tomographic image and said fluoroscopic image are displayed in parallel on said display.

9. The CT imaging method according to claim 8, wherein said second position setting step receives the designation to set said second position while a position index indicating said first position is displayed on said panoramic tomographic image displayed on said display.

10. The CT imaging method according to claim 7, wherein said first position setting step displays a range index indicating a range of said imaging region on said panoramic tomographic image displayed on said display.

11. The CT imaging method according to claim 7, wherein said second position setting step displays a range index indicating a range of said imaging region on said fluoroscopic image displayed on said display.

12. The CT imaging method of claim 7, further comprising a panoramic imaging executing step that executes panoramic imaging for acquiring said panoramic tomographic image.

13. An information processing method of processing information causing an X-ray imaging apparatus to execute X-ray imaging, said information processing method comprising:
  displaying a panoramic tomographic image of a dental arch of a subject on a display;
  receiving an input of a designation operation to designate a position in a mesiodistal direction on said panoramic tomographic image displayed on said display in said panoramic tomographic image displaying step, and setting a first position on said panoramic tomographic image based on the designation operation;
  providing information executing X-ray imaging for acquiring a fluoroscopic image by irradiating said subject with an X-ray beam along a fluoroscopic imaging direction having a tangential direction component at said first position on said panoramic tomographic image set in said first position setting step to said X-ray imaging apparatus;
  displaying said fluoroscopic image acquired by said X-ray imaging apparatus on said display;
  receiving an input of a designation operation to designate a position in a buccolingual direction on said fluoroscopic image displayed on said display in said fluoroscopic image displaying step, and setting a second position based on the designation operation;
  setting an imaging region of CT imaging based on said second position set in said second position setting step; and
  providing information executing said CT imaging by irradiating said imaging region set in said imaging region setting step with an X-ray cone beam to the X-ray imaging apparatus capable of executing the CT imaging.

14. A non-transitory recording medium having a computer-readable program recorded on the medium, said program causing a computer to execute:
  displaying a panoramic tomographic image of a dental arch of a subject on a display;
  receiving an input of a designation operation to designate a position in a mesiodistal direction on said panoramic tomographic image displayed on said display in said panoramic tomographic image displaying step, and setting a first position on said panoramic tomographic image based on the designation operation;
  providing information executing X-ray imaging for acquiring a fluoroscopic image by irradiating said subject with an X-ray beam along a fluoroscopic imaging direction having a tangential direction component at said first position on said panoramic tomographic image set in said first position setting step to an X-ray imaging apparatus;
  displaying said fluoroscopic image acquired by said X-ray imaging apparatus on said display;
  receiving an input of a designation operation to designate a position in a buccolingual direction on said fluoroscopic image displayed on said display in said fluoroscopic image displaying step, and setting a second position based on the designation operation;
  setting an imaging region of CT imaging based on said second position set in said second position setting step; and
  providing information executing said CT imaging by irradiating said imaging region set by said second position setting step with an X-ray cone beam to the X-ray imaging apparatus capable of executing the CT imaging.

* * * * *